United States Patent
Thompson, Jr. et al.

(10) Patent No.: US 9,283,055 B2
(45) Date of Patent: Mar. 15, 2016

(54) METHOD FOR ESTABLISHING DRILL TRAJECTORY FOR DENTAL IMPLANTS

(71) Applicant: FPJ Enterprises, LLC, Cornelius, NC (US)

(72) Inventors: Fredrick C. Thompson, Jr., Davidson, NC (US); Paul Alan Crandall, Cornelius, NC (US); Jennifer T. Strong, Davidson, NC (US)

(73) Assignee: FPJ Enterprises, LLC, Cornelius, NC (US)

( * ) Notice: Subject to any disclaimer, the term of this patent is extended or adjusted under 35 U.S.C. 154(b) by 0 days.

(21) Appl. No.: 14/832,126

(22) Filed: Aug. 21, 2015

(65) Prior Publication Data

US 2015/0351866 A1    Dec. 10, 2015

Related U.S. Application Data

(63) Continuation-in-part of application No. PCT/US2015/045515, filed on Aug. 17, 2015, and a continuation-in-part of application No. 14/487,515, filed on Sep. 16, 2014, now abandoned.

(Continued)

(51) Int. Cl.
*A61C 3/00* (2006.01)
*A61C 1/08* (2006.01)
(Continued)

(52) U.S. Cl.
CPC .............. *A61C 1/084* (2013.01); *A61B 19/50* (2013.01); *A61C 8/0089* (2013.01); *A61C 9/004* (2013.01); *A61B 2019/502* (2013.01)

(58) Field of Classification Search
CPC .. A61B 17/17; A61B 17/1703; A61B 17/171; A61B 17/1732; A61B 17/176; A61C 1/082; A61C 1/084; A61C 1/085; A61C 1/10; A61C 1/12
USPC ................... 433/72–76, 172–176; 606/96–97
See application file for complete search history.

(56) References Cited

U.S. PATENT DOCUMENTS

| | | |
|---|---|---|
| 2,412,594 A | 12/1946 | Antonidis |
| 3,011,259 A | 12/1961 | Baum |

(Continued)

FOREIGN PATENT DOCUMENTS

| | | |
|---|---|---|
| FR | 2878429 A1 | 6/2006 |
| WO | 2009094576 A1 | 7/2009 |
| WO | 2012076574 A2 | 6/2012 |

OTHER PUBLICATIONS

Zimmer, Ingo, Cerec Guide, Mar. 29, 2012, 20 pages, Sirona Dental Systems GMBH, Bensheim, Germany.

(Continued)

*Primary Examiner* — Yogesh Patel
(74) *Attorney, Agent, or Firm* — Kevin E. Flynn; Flynn IP Law

(57) ABSTRACT

Aligning a drill bit for preparing a bore to receive a dental implant. Using a frame to position cartridges, the frame fitting patient anatomy and having a chamber to receive cartridges. Creating an initial cartridge with an opening to receive a guide sleeve. Optionally, mounting at least one measuring device assembly onto the initial assembly so that measuring device assembly takes measurements with a known relationship to the initial linear trajectory. Using the measurements to enhance a model of the surgical site and to select a surgical linear trajectory for a surgical bore to stay within bone found at the surgical site. Placing a surgical cartridge into the chamber; and placing a guide sleeve in the surgical cartridge with the guide sleeve oriented along the surgical linear trajectory to constrain a drilling trajectory of a drill bit along the surgical trajectory. Many variations disclosed.

30 Claims, 21 Drawing Sheets

Related U.S. Application Data

(60) Provisional application No. 61/973,809, filed on Apr. 1, 2014, provisional application No. 62/046,572, filed on Sep. 5, 2014, provisional application No. 62/074,550, filed on Nov. 3, 2014, provisional application No. 62/074,577, filed on Nov. 3, 2014, provisional application No. 62/074,519, filed on Nov. 3, 2014, provisional application No. 62/113,352, filed on Feb. 6, 2015.

(51) Int. Cl.
  *A61C 8/00* (2006.01)
  *A61C 9/00* (2006.01)
  *A61B 19/00* (2006.01)

(56) References Cited

U.S. PATENT DOCUMENTS

| | | |
|---|---|---|
| 5,015,183 A | 5/1991 | Fenick |
| 5,183,414 A | 2/1993 | Czerniawski |
| 5,246,370 A | 9/1993 | Coatoam |
| 5,302,122 A | 4/1994 | Milne |
| 5,320,529 A | 6/1994 | Pompa |
| 5,556,278 A | 9/1996 | Meitner |
| 5,613,852 A | 3/1997 | Bavitz |
| 5,718,579 A | 2/1998 | Kennedy |
| 5,725,376 A | 3/1998 | Poirier |
| 5,769,636 A | 6/1998 | Di Sario |
| 5,800,168 A | 9/1998 | Cascione |
| 5,888,034 A | 3/1999 | Greenberg |
| 5,888,065 A * | 3/1999 | Sussman .............. A61C 1/084 433/76 |
| 5,915,962 A | 6/1999 | Rosenlicht |
| 5,941,706 A | 8/1999 | Ura |
| 5,954,769 A | 9/1999 | Rosenlicht |
| 5,967,777 A | 10/1999 | Klein |
| 5,989,025 A | 11/1999 | Conley |
| 6,296,483 B1 | 10/2001 | Champleboux |
| 6,319,006 B1 | 11/2001 | Scherer |
| 6,634,883 B2 | 10/2003 | Ranalli |
| 6,814,575 B2 | 11/2004 | Poirier |
| 6,869,283 B2 | 3/2005 | Sussman |
| 6,926,525 B1 | 8/2005 | Ronvig |
| 6,966,772 B2 | 11/2005 | Malin |
| 7,014,461 B2 | 3/2006 | Weinstein |
| 7,044,735 B2 | 5/2006 | Malin |
| 7,086,860 B2 | 8/2006 | Schuman |
| 7,097,451 B2 | 8/2006 | Tang |
| 7,322,821 B1 | 1/2008 | Lin |
| 7,331,786 B2 | 2/2008 | Poirier |
| 7,429,175 B2 | 9/2008 | Gittelson |
| 7,654,823 B2 | 2/2010 | Dadi |
| 7,695,279 B2 | 4/2010 | Hirsch |
| 7,845,943 B2 | 12/2010 | Meitner |
| 7,854,611 B2 | 12/2010 | Yau |
| 7,905,726 B2 | 3/2011 | Stumpel |
| 7,950,924 B2 | 5/2011 | Brajnovic |
| 8,011,927 B2 | 9/2011 | Berkmans |
| 8,021,150 B2 | 9/2011 | Fuentevilla |
| 8,038,440 B2 | 10/2011 | Swaelens |
| 8,105,081 B2 | 1/2012 | Bavar |
| 8,142,189 B2 | 3/2012 | Brajnovic |
| 8,157,563 B2 | 4/2012 | Brajnovic |
| 8,170,327 B2 | 5/2012 | Glor |
| 8,215,957 B2 | 7/2012 | Shelton |
| 8,221,121 B2 | 7/2012 | Berkmans |
| 8,246,352 B2 | 8/2012 | Takebayashi |
| 8,257,083 B2 | 9/2012 | Berkmans |
| 8,333,587 B2 | 12/2012 | Jamison |
| 8,348,669 B1 | 1/2013 | Schmitt |
| 8,364,301 B2 | 1/2013 | Schmitt |
| 8,366,442 B2 | 2/2013 | Schmitt |
| 8,382,475 B2 | 2/2013 | Stein |
| 8,398,396 B2 | 3/2013 | Taormina |
| 8,414,296 B2 | 4/2013 | Berkmans |
| 8,523,566 B2 | 9/2013 | Suter |
| 8,535,055 B2 | 9/2013 | Katz |
| 8,540,510 B2 | 9/2013 | Brajnovic |
| 8,582,870 B2 | 11/2013 | Glor |
| 8,585,402 B2 | 11/2013 | Vogel |
| 8,651,858 B2 | 2/2014 | Berkmans |
| 8,690,569 B2 | 4/2014 | Machado |
| 8,708,699 B2 | 4/2014 | Suter |
| 8,714,975 B2 | 5/2014 | Stumpel |
| 8,764,440 B2 | 7/2014 | Haber |
| 8,777,613 B2 | 7/2014 | Wolf |
| 8,794,963 B2 | 8/2014 | Lancieux |
| 8,794,964 B2 | 8/2014 | Haber |
| 8,808,000 B2 | 8/2014 | Salcedo |
| 8,827,699 B2 | 9/2014 | Bavor |
| 8,827,704 B2 | 9/2014 | Sanders |
| 8,858,228 B2 | 10/2014 | Katz |
| 8,870,574 B2 | 10/2014 | Berkmans |
| 8,888,488 B2 | 11/2014 | Berkmans |
| 8,897,526 B2 | 11/2014 | MacLeod |
| 8,954,181 B2 | 2/2015 | MacLeod |
| 8,956,158 B2 | 2/2015 | Schmalzle |
| 9,011,148 B2 | 4/2015 | Dolfi |
| 9,039,413 B2 | 5/2015 | Suter |
| 2004/0219479 A1 | 11/2004 | Malin |
| 2005/0170311 A1 | 8/2005 | Tardieu |
| 2007/0154862 A1 | 7/2007 | Kim |
| 2008/0166681 A1 | 7/2008 | Weinstein |
| 2009/0004625 A1 * | 1/2009 | Esposti ............... A61B 17/1673 433/165 |
| 2009/0136902 A1 | 5/2009 | Zundorf |
| 2009/0187393 A1 | 7/2009 | Lierde |
| 2009/0202959 A1 | 8/2009 | Ajlouni et al. |
| 2009/0274990 A1 | 11/2009 | Kim |
| 2009/0316966 A1 | 12/2009 | Marshall |
| 2009/0325128 A1 | 12/2009 | Holzner |
| 2010/0129768 A1 | 5/2010 | Isidori |
| 2010/0145898 A1 | 6/2010 | Malfliet |
| 2010/0173259 A1 * | 7/2010 | Vogel ..................... A61C 1/084 433/72 |
| 2010/0255441 A1 * | 10/2010 | Taormina ............... A61C 1/084 433/75 |
| 2010/0256649 A1 | 10/2010 | Capsal |
| 2010/0323320 A1 * | 12/2010 | Takebayashi .......... A61C 1/084 433/75 |
| 2011/0111371 A1 | 5/2011 | Haber |
| 2011/0208195 A1 | 8/2011 | Palti |
| 2011/0238071 A1 | 9/2011 | Fernandez-Scoma |
| 2011/0287379 A1 | 11/2011 | Lal |
| 2012/0178043 A1 | 7/2012 | Haber |
| 2012/0300908 A1 | 11/2012 | Mayer |
| 2012/0319859 A1 | 12/2012 | Taub |
| 2013/0071811 A1 | 3/2013 | Groscurth |
| 2013/0302752 A1 | 11/2013 | Schneider |
| 2013/0309628 A1 | 11/2013 | Orth |
| 2013/0316298 A1 | 11/2013 | Ikegami |
| 2014/0026419 A1 | 1/2014 | Haber |
| 2014/0162213 A1 | 6/2014 | Haber |
| 2014/0193772 A1 | 7/2014 | Mackey |
| 2014/0234803 A1 | 8/2014 | Hehn |
| 2015/0030995 A1 | 1/2015 | Villa |
| 2015/0196372 A1 | 7/2015 | Champleboux |

OTHER PUBLICATIONS

SAFEGIDE Instructions, 2013, 3 pages, Safegide, La Jolla, California, USA.
Basic Techniques Slideshows, 2011, 3 pages, DePlaque, Victor, New York, USA.
i4 Surgical Guide Instructions on Model Planning, 2 pages, Mar. 12, 2014, innoDent Surgical Guides, Colorado Springs, Colorado, USA.
Manikandan Ramasamy, GIRI, Implant surgical guides: From the past to the present, Journal of Pharmacy & BioAllied Sciences (J Pham Bioallied Sci. Jun. 2013; 5(Suppl 1): S98-S102), Jun. 2013, 7 pages, Medknow Publications and Media Pvt. Ltd., part of Wolters Kluwer Health, Mumbai, India.
Kola, Mohammed Zaheer, Surgical Templates for Dental Implant Positioning; Current Knowledge and Perspectives, Nigerian Journal

(56) References Cited

OTHER PUBLICATIONS of Surgery (Niger J Surg. Jan.-Jun. 2015; 21(1):1-5), 6 pages, Nigerian Surgical Research Society and the Association of Surgeons of Nigeria, Nigeria.
Ossfit(R) One Surgical Step: Surgical Guide, Feb. 2013, 48 pages, Anthogyr, Sallanches, France.
Sicat Implant Sicat Surgical Guides, Jan. 6, 2013, 56 pages Sicat GMBH & Co. KG, Bonn Germany.
Radiographic/Surgical Guides, obtained from http://www.njperioimplant.com/referring-doctors/radiographicsurgicalguides/ on Jun. 17, 2015, (13 pages as printed including some pages with just banner) Periodontics and Oral Medicine, PA, Livingston, New Jersey, USA.
Scanning Protocols for Implant Cases, May 31, 2013, 7 pages, InPronto, Inc., San Francisco, California, USA.
Cone Beam Implant Planning Manual, Jan. 3, 2012, 12 pages, available online at http://www.dentalimplantplanning.com/CT%020Scan%20Protocol.pdf, ROE Dental Laboratory, Garfield Heights, Ohio, USA.
Anatomage Guide A Surgical Guide exclusively for Invivo5, http;//www.anatomage.com/dental-products/surgical-guide, downloaded Jun. 17, 2015, 9 pages, Anatomage, San Jose, California, USA.
GuideMia Treatment Planner, downloaded Jun. 16, 2015, 3 pages, GuideMia, Cypress, California, USA.
Guided Surgery, copyrighted 2015, downloaded Jun. 16, 2015 3 pages (but augmented with 4 pages of screen prints), found at http://www.3ddx.comiguided_surgery.html, 3D Diagnostix, Inc., Boston, Massachusetts, USA.
Inho, Han, Written Opinion of the International Searching Authority for PCT/US2015/045535 (related application), Nov. 20, 2015, 8 pages, Korean Intellectual Property Office, Daejeon, Republic of Korea.
Inho, Han, Corrected Version of Written Opinion of the International Searching Authority for PCT/US2015/045515 (priority document for the present application), Dec. 1, 2015, 6 pages, Korean Intellectual Property Office, Daejeon, Republic of Korea.

* cited by examiner

Prior Art <u>1000</u>

| 1010 | Create Treatment Plan |
| 1020 | Data Collection to Fabricate Surgical Guide |
| 1030 | Import Data into Planning Software |
| 1040 | Case Planning |
| 1050 | Electronic Transfer |
| 1060 | Guide Manufacture |
| 1070 | Shipping & Delivery |
| 1080 | Attempt of Surgery Using Guide |

400

280

METHOD FOR ESTABLISHING DRILL TRAJECTORY FOR DENTAL IMPLANTS

This application claims priority to a series of earlier filed United States patent applications and one PCT application either directly to currently co-pending applications or through a series of one or more links from co-pending applications. All applications claimed for priority are incorporated by reference.

PCT Application No. PCT/US15/45515 filed Aug. 17, 2015 for System of Establishing Drill Trajectory for Dental Implants.

U.S. patent application Ser. No. 14/487,515 filed Sep. 16, 2014 for Dental Implant System and Method.

U.S. Provisional Patent Application No. 61/973,809 filed Apr. 1, 2014 for Dental Implant System and Method.

U.S. Provisional Patent Application No. 62/046,572 filed Sep. 5, 2014 for Cartridge with Irrigation.

U.S. Provisional Patent Application No. 62/074,550 filed Nov. 3, 2014 for Hex Sleeve with Soft Tissue Pin.

U.S. Provisional Patent Application No. 62/074,577 filed Nov. 3, 2014 for X-Ray Holder Apparatus and Method.

U.S. Provisional Patent Application No. 62/074,519 filed Nov. 3, 2014 for Guide Sleeve Apparatus and Method.

U.S. Provisional Patent Application No. 62/113,352 filed Feb. 6, 2015 for System for 3D Planning, Verification, Guiding and Validating the Placement of a Dental Implant.

BACKGROUND

Field of the Disclosure

This disclosure relates generally to tools, systems, and methods for preparing a bore hole in a patient's mouth to receive a dental implant.

Word Usage.

Align or Alignment. Placed in a prescribed relationship. Thus an object is aligned to another object if set in a particular orientation relative to the another object. The relationship may be co-linear, parallel, perpendicular, or any other prescribed relationship.

Co-Linear, Parallel or Perpendicular. Relationships between various items including various linear trajectories and components are described with words so as co-linear, parallel, or perpendicular. There are many variations such as a plane containing a trajectory. Those of skill in the art will recognize that such relationships are unlikely to be absolutely co-linear, parallel, perpendicular, or otherwise as this is not a discussion of mathematics but work within the constraints of working within a mouth of a patient. The relationships have been described to enable the teachings to those of skill in the art. Thus these terms should be interpreted as commercially reasonable efforts to achieve the goal of co-linear, parallel, or perpendicular unless the specification or claims specifically state that a relationship is absolutely co-linear, absolutely parallel, or absolutely perpendicular. Devices built with insubstantial differences from absolute relationships but remain substantially as taught for the relevant relationships are practicing the teachings of the present disclosure.

Implant—In the context of this application, a dental implant or simply an implant or sometimes an endosseous implant is a surgical component the interfaces with the bone of the jaw to act as an orthodontic anchor for a dental prosthesis such as a crown that covers the implant rather than an existing tooth to form a prosthetic tooth. Other prosthetic devices such as bridges, dentures, may be connected to one or more implants. Typically, an abutment is placed on the implant and the dental prosthesis is then connected to the abutment. An implant may support a single prosthetic tooth. One implant may support more than one prosthetic tooth. Several implants may be used to support a larger prosthetic.

Or.—Unless explicit to the contrary, the word "or" should be interpreted as an inclusive or rather than an exclusive or. Thus, the default meaning of or should be the same as the more awkward and/or.

STL—STereoLighography is a file format used with stereolithography CAD software. The STL file format is used for rapid prototyping, three-dimensional printing, and computer-aided manufacturing.

Directions in Dentistry

Given that dentistry works an upper jaw (maxilla) and a lower jaw (mandible) and works with a curved array of teeth, the standard medical terms of superior/inferior cephalad/caudal or anterior/posterior are not helpful outside of a specific context. Thus the directions are typically conveyed as:

apical (toward root tip) versus coronal (toward crown) or sometimes occlusal (towards biting surface for posterior teeth) or incisal (towards biting surface for anterior teeth);

buccal (cheek side) or labial (lip side) or sometimes more generally as facial (either buccal or labial) versus lingual (tongue side) or palatal (towards palate); and distal (towards last tooth in quadrant) versus mesial (towards midline).

As there are two different possible words for inside the array of teeth (lingual and palatal) and at least three possible words for outside the array of teeth (buccal, labial, facial), this application will simply use inner-outer.

Introduction to Environment.

Dental implants are known in the art. Implants are used to anchor various prosthetic devices. The implant is frequently placed into a bore hole in a jaw of the patient. Placement of the bore hole is important as the bore hole must be sufficient to provide the needed capacity to receive the implant but must also be placed so as to avoid doing damage to the patient. Thus the drill trajectory for the bore hole should afford sufficient bone clearance on all sides so there is sufficient bone to retain the implant and the drill trajectory does not damage nearby tooth roots, nerves, or the sinus cavity. As there is considerable variation in anatomy between patients, the task of selecting an appropriate drill trajectory is not an easy task.

In order to appreciate the many teachings of this disclosure provided below, it is helpful to review a prior art process for preparing a patient's mouth to receive a dental implant by drilling a bore on a planned drill trajectory. The planned implant trajectory is something created within the planning software to compromise the ideal trajectory for restorative and aesthetic purposes to make modifications in light of the anatomic features as viewed in the virtual model of the implant site within the planning system software.

FIG. 1 shows a flow chart for a prior art method 1000 to create a bore for receipt of a dental implant. A surgical guide (sometimes called surgical template) is created to guide the drilling system used to create the bore to receive the implant. The surgical guide may be made based upon computer images of the treatment area so that that the surgical guide is custom fit for use in the patient's mouth.

The surgical guide can be said to have two main components, the guide sleeves and the contact surface. The contact surface provides a custom fit with the patient's mouth (gums, jawbone, and teeth). One or more guide sleeves (sometimes guide cylinders) within the drill guide are used to orient and guide the drilling system to create a bore at the desired location and with the desired angulation (distal-mesial and inner-outer). The goal is to get the bore for the implant created so that the apical end of the bore and all sides of the bore are fully enclosed in bone. Further, the drilling should not damage nearby anatomic structures, including nerves or roots of adjacent teeth. The implant placement should be compatible with the intended prosthetic solution and not complicate the creation of the prosthetic solution to compensate for an awkward placement of the implant.

Step 1010—Create Treatment Plan. The dentist weighs patient needs, anatomic conditions, and patient objectives to determine a treatment plan. The inputs may include photos, dental impressions, X-ray images, and an examination by the dentist. Depending on the conditions within the patient's mouth and the treatment plan one of several types of surgical guides are selected. The basic details of the four most common types of surgical guides are:

Tooth-Supported Guide.
Guide coverage will rest over patient's existing dentition;
Single tooth, multi-unit bridge, or partially edentulous cases;
Minimally invasive procedure;
Can require patient scan, optical scan of stone model or digital impression, and any wax up prosthesis that you would like to include in the planning phase; and
With most systems is Single Scan technique.
Mucosa-Supported Guide.
Guide coverage will rest on the patient's soft tissue;
Fully edentulous cases only;
Minimally invasive procedure;
Anchor pins for guide fixation;
Requires patient scan wearing radiopaque duplicate denture, scan of duplicate denture by itself, optical scan of edentulous arch stone model or digital impression; and
With most systems is Double Scan technique.
Bone-Supported Guide.
Guide coverage will rest on bone surface of arch after soft tissue flap has been reflected;
Fully edentulous cases only;
Anchor pins for guide fixation;
Requires patient scan and denture scan; and
With most systems is Single Scan technique;
Bone Reduction Guide.
Guide coverage will rest on bone surface of arch after soft tissue flap has been reflected;
First guide: acrylic opening on surgical guide will guide level of bone reduction;
Second guide: sits on post-reduced ridge to guide implant osteotomy;
Fully edentulous mandibular cases only;
Anchor pins for guide fixation;
Requires patient scan and denture scan; and
With most systems is Single Scan technique.

The selection process and use of the above-identified surgical guides are well-known in the art and need no further explanation.

Step 1020 Data Collection to Fabricate Surgical Guide.

In order to plan a surgery using a surgical guide data must be gathered to be used in designing the guide superstructure and the location and angle of the guide sleeves within the superstructure. The super structure provides for proper fit and retention at the surgical site and the housing of the guide sleeves. The guide sleeves provide the proper orientation of drilling. Multiple versions of this step are available depending on the software used. The two most common versions are defined as; single scan and dual scan. Both of these versions require at least one CBCT scan of the patient. The output from the CBCT scan is often a DICOM file.

Single Scan Technique
The patient has a CBCT scan taken of the surgical site without a scan appliance. Depending on the system, this technique is most commonly used with partially edentulous arches, bone supported guides and bone reduction guides. Due to the guide resting on teeth or bone this information is more accurately mapped by the CBCT scan than soft tissue. STL files from intraoral scans or model scans can also be overlaid more accurately than edentulous cases.

Dual Scan Technique.
The patient has a CBCT scan taken of the surgical site with a scan appliance.

The dual scan technique is most commonly used with fully edentulous arches. Due to the guide resting on mobile soft tissue, there is inaccurate information mapped by the CBCT scan.

STL files from intraoral scans or model scans can also be overlaid for more accurately planning the edentulous cases. The scan appliance (sometimes scan prosthesis) has fiduciary markers that help to visualize the desired tooth set-up in the CT and CBCT three-dimensional images. Sometimes the fiduciary markers are simply a radiopaque liner applied to the interior surface of denture. These images help to determine how to place the patient's implants from a clinical as well as an esthetic point of view. For a mucosa-supported guide, it's the scan appliance that makes it possible to fabricate the guide.

Data gathered for the different types of appliances:
Tooth-Supported Surgical Guide-Using Impression
Take impression;
Make bite index or spacer;
Make stone model/extract teeth if needed;
Make wax-up;
Optical scans from stone model with or without wax-up; and
CBCT scan of patent with bite index.
Tooth-Supported Surgical Guide-Using Intraoral Scan.
Take intra-oral scan;
Make bite index or spacer;
Digital tooth set-up; and
CBCT scan of patent with bite index.
Fully edentulous arch; Mucosa-Supported Guide or Bone-Supported Guide, or Bone Reduction Guide.
Fabricate scan appliance; create a new or reline recent prosthesis and add fiduciary markers
Make a bite index
Scan 1; CBCT scan with the patient, scan appliance and bite index
Scan 2 CBCT scan of the scan appliance by itself A bite index is useful in that it shows the relationship of the biting surfaces and thus indicates the relationship between the two jawbones. A bite index in a fully edentulous arch is taken with the dentures in place to capture how one jawbone is oriented relative to the other jawbone.

A wax up is made on the stone model. The wax up is a practical representation of the position and shape of the prosthetic tooth. Some planning systems skip the creating of wax up and simply use a virtual tooth in the model.

Step 1030—Import Data into Planning Software.

The data collected has to be merged in a format that is readable by the implant surgery guide planning software. Depending on the software that is being utilized, the case type and the surgical guide type there can be different steps to accomplish this. The common steps are listed for various surgical guide types. Those of skill in the art will recognize that particular implementations of planning software and preferences may mean that additional data files are obtained and loaded.

Tooth-Supported Surgical Guide.
Import CBCT
Import digital scan or scans
Fully Edentulous Arch.
Import CBCT scan with the patient, scan appliance and bite index
Import CBCT scan of the scan appliance by itself
Step 1040—Case Planning.

The location and trajectory of the implant or implants is selected within a virtual model of the patient's mouth. The planning software is used to plan the location, depth and angulation of the implant.

The three-dimensional information that has been imported into the software is displayed two-dimensionally. The user selects two-dimensional slices that show the surgical location or locations. These slices demonstrate the availability of bone volume in that area.

In addition to the available bone volume the user may be able to view a proposed restorative space in that slice. This restorative space can be represented by the digital scan of a wax up, the scan appliance or a digitally created tooth. If there is no restorative space represented then the user locates and angles the implant to a position that looks best in the hard tissue and guesses the proper restorative angulation of the implant. If the software provides a restorative space then the user picks the best angle and location of the implant that matches the bone volume and restorative space. This position is subjective and there is no accurate or practical method to measure the proposed implant location to other anatomical landmarks. Most software does not demonstrate or include the user in planning the framework of the guide.

Step 1050—Electronic Transfer.

The data for the surgical plan is electronically transferred to the lab. The lab designs and manufactures the surgical guide.

Step 1060—Guide Manufacture.

The lab creates the surgical guide using manufacturing techniques which may include work by hand, milling, CAD/CAM methods, or other methods known to those of skill in the art. The surgical guide receives one or more guide sleeves to attempt to reproduce the positioning and angulation of the implants based upon results of case planning and the surgery as envisioned in the virtual model.

Step 1070—Shipping & Delivery.

The completed surgical guide is then delivered to the appropriate office for surgery. There is no practical method for the user to evaluate the guide for fit or accuracy prior to surgery.

Step 1080—Attempt at Surgery Using Guide.

Depending on the number of implants the dental office blocks out of their schedule one to four hours for the procedure. The surgical guide is secured at the surgical site and drilling is performed according to implant protocol.

In most instances, no verification is done to ensure that the surgical guide and guide sleeves were manufactured and now positioned so as to accurately guide the drilling process to achieve the precise implant placement from the virtual model. In many instances there is not a viable way to make such a check.

In some instances, a dental office with a CBCT scanner can anesthetize a patient, secure the surgical guide, and then transport the patient from the treatment room to an imaging room at the facility with the CBCT scanner. Even for the relatively small fraction of dental facilities that have a CBCT scanner as of the writing of this disclosure, the added steps and time requirements are daunting.

Even with a CBCT scanner, it is not clear what a dentist would do with that information given that there are not many options to allow the surgical guide to be adjusted. In the case of miss-positioning of the surgical guide within the mouth of the patient, this error could be caught and corrected. However, when the surgical guide is repositioned, another CBCT scan would be needed to confirm that the implant trajectory established by the surgical guide matches the desired implant trajectory from the planning software. The problems tend to be more with the surgical guides for the lower jaw as surgical guides for the upper jaw tend to be easier to reliably insert as the surgical guide is locked in place by conforming to the palate.

The source of the problem may have been improper positioning of the patient during the CBCT scan used during the planning process as the planning software makes certain assumptions about the orientation of the patient with respect to the CBCT scan.

The source of the problem may be an error made during the process of planning the implant trajectory as the process may allow substantial latitude to the dentist to move the implant trajectory in any direction or change angulation in any direction. Some choices may not be what the dentist really intended. As the surgical guide is not made in the presence of the dentist, the error may not be caught until the patient is back at the dental office and ready for the implant to be placed.

Sometimes the process by the dentist and the implant planning software was flawless and the error is simply a manufacturing error of the surgical guide.

Sometimes the process by the dentist and the implant planning software was flawless and the surgical guide was accurately made to the requested specification but in a period of weeks between the visit by the patient to provide the images used in the planning process and the visit for the surgical guide to be used, the patient's mouth has deteriorated or otherwise changed so that the old plan is no longer applicable.

Thus, for a number of reasons, a surgical guide may be inappropriate and not provide a desired implant trajectory for drilling. If the surgical guide is rejected in favor of a new guide, the planning steps may need to be repeated (especially if it is not immediately clear what caused the problem with the surgical guide). This means that the dental practice loses productivity for the procedure room and team assembled to drill and place the implant. The patient is inconvenienced by having to schedule another visit several weeks out. This need to scrap the surgical guide is likely to cause the patient to doubt the process or the dentist and wonder just how accurate the next surgical guide will be. If the lab has a fair number of surgical guides that must be done over, that loss of revenue will be passed along in higher prices for the surgical guides.

Note—there is no guarantee that a second surgical guide will be free from the problems listed above. It is possible that this second guide may not be suitable as well. Because of the problems with surgical guides not being reliable over 90 percent of dentists perform single implant surgeries without a surgical guide. This is remarkable given that placement of dental implants and the selection of implant trajectories to create a bore for use with a dental implant is a difficult task given that the variations amongst patients makes necessary to establish an implant trajectory for each procedure. Thus, even if two patients with the same gender, age, and size needed implants in the same numbered tooth position, the dentist would not be able to blindly re-use the implant trajectory from the first patient on the second patient. One study indicated that even after going through the process to make a surgical guide, 15 to 20 percent of the cases discarded the surgical guide and did the drilling without a surgical guide.

If the surgical guide is actually used to guide the drilling process, then frequently the guide sleeve is augmented with another sleeve that fits within the guide sleeve so that a small diameter drill bit may be used initially followed by one or more intermediate diameter drill bits and finally a final drill bit that is used with the guide sleeve without any inner sleeve. Frequently the process is cooled by spraying water on the drill bit although this process is less than desirable in that is requires an assistant to attempt to spray irrigant towards the drill bit through a window which is not easy given there is limited room for hands and devices within the patient's mouth.

United States Patent Application Publication No. 2013/0302752 for Dental Impression, Drilling Template and Method for Providing A Relative Location for Creating a Drilling Template is relevant to this discussion. The '752 places impression compound around the surgical site and adjacent anatomy. A positioning aid 4 is placed into the impression compound. An apical portion of the positioning aid 4 will leave a negative impression in the impression compound. The apical portion 5 is not round so the positioning aid is not free to rotate around an apical to coronal axis of the positioning aid after the impression compound has hardened. The shape of the apical portion 5 also precludes removing the positioning aid and placing the positioning aid back into hardened impression compound at a rotational position different from the initial rotational position. The positioning aid is adapted to be visible in an MRI image or X-ray image and the impression compound cures to be radiolucent.

After processing data obtained from an image obtained with the positioning aid 4 in place, a drilling direction is selected relative to the negative impression of the apical part of the positioning aid 4 (called a connecting part 7). A drill guide 8 is created to fit an apical portion of the drill guide 8 within the void left by the positioning aid 4 and limits the drill guide 8 to a single orientation. A bore 9 through the drill guide 8 may be used to guide a series of drill bits of increasing sizes by a placing series of sleeves 12 in the bore 9 to constrict the effective inner diameter of the bore 9.

The drill guide 8 is made from an ablative process such as grinding or milling to remove material from a block having a pre-formed bore. One can appreciate that the block would need to be of a material of sufficient hardness and heat tolerance to serve as a limit on a rapidly spinning shaft of a drill bit while maintaining dimensional integrity so as to continue to limit the movement of the drill bit shaft relative to the desired drilling direction.

Thus, to avoid having a delay while a file is sent offsite to create the drill guide 8, a milling machine or other precision machining tool must be present to operate under computer control. This is a large expense for a dental office. An added expense is the coast of the blanks with pre-formed bores and block brackets 17 for engagement with the ablating device (See FIG. 7 or FIG. 8).

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Some of the teachings of the present disclosure may be summarized as a method of aligning a drill bit for preparing a bore to receive a dental implant. The method including creating a three-dimensional model of the surgical site and selecting an initial linear trajectory for drilling an initial planned bore. Creating a frame to position a cartridge coronal to the surgical site, the frame prepared to fit patient anatomy adjacent to the surgical site and having a chamber to receive the cartridge. Creating an initial cartridge with an opening from a coronal side of the initial cartridge to an apical side of the initial cartridge.

Placing the initial cartridge into the chamber and placing a guide sleeve in the opening in the initial cartridge to form an initial assembly. The opening in the initial cartridge designed to constrain the orientation of the guide sleeve so that a longitudinal axis of a coronal to apical bore in the guide sleeve is positioned a known offset from the initial linear trajectory.

Obtaining measurements from a measuring device assembly with a known relationship to the initial linear trajectory, preferably by mounting the at least one measuring device assembly onto the initial assembly. Using the measurements to enhance the three-dimensional model of the surgical site. Selecting a surgical plan for a surgical bore with an apical end, a coronal end, a diameter, and a surgical linear trajectory. The surgical bore selected to stay within a bone volume found at the surgical site.

Placing a surgical cartridge into the chamber of the frame; and placing a guide sleeve in the surgical cartridge; the guide sleeve constrained by a coronal to apical opening in the surgical cartridge so that a longitudinal bore in the guide sleeve is oriented along the surgical linear trajectory such that the guide sleeve may be used to constrain a drilling trajectory of a drill bit along the surgical trajectory. Many variations and alternatives are disclosed.

Some of the teachings of the present disclosure may be summarized as an alignment assembly for aligning a drill bit used to create a bore apically into bone as part of a process to prepare a bore for receipt of a dental implant. The assembly having a frame created from a first additive manufacturing process so that the frame does not need to cure while positioned within the patient's mouth. The frame created to at least partially conform to patient anatomy adjacent to a surgical site that will receive the bore; the frame having a chamber to receive a series at least one cartridges. The assembly having a guide sleeve having a coronal to apical bore with at least a portion of the bore sized to constrain a drill bit to promote drilling along a centerline of the coronal to apical bore of the guide sleeve. The assembly having a cartridge created from a second additive manufacturing process. The cartridge adapted to fit within the frame such that the frame constrains the cartridge from movement other than a removal of the cartridge. The cartridge having a coronal-apical opening for receipt of the guide sleeve to position the centerline of the coronal to apical bore of the guide sleeve co-linear with a desired linear trajectory for aligning the drill bit used to create the bore.

The first and second additive manufacturing process may be the same process or different processes.

Some of the teachings of the present disclosure may be summarized as a method of irrigating a drilling process within a jawbone of a patient. The method providing a set of substantially aligned bores through a frame and cartridge. Providing a set of at least one opening in the guide sleeve to provide an access channel for irrigation fluids to be provided to a drill bit constrained by the guide sleeve, the drill bit to guide sleeve interaction designed to allow for apical travel of the irrigation fluids. Providing irrigation fluids to the substantially aligned bores, preferably, whenever the drill bit is driven by a drill bit drive.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. The lack of scale is particularly present in the many figures that show a series of components rather than assemblies so that the individual components may be appreciated. Moreover, in the figures, like reference numerals designate corresponding parts throughout the different views.

DETAILED DESCRIPTION

Figure 1:
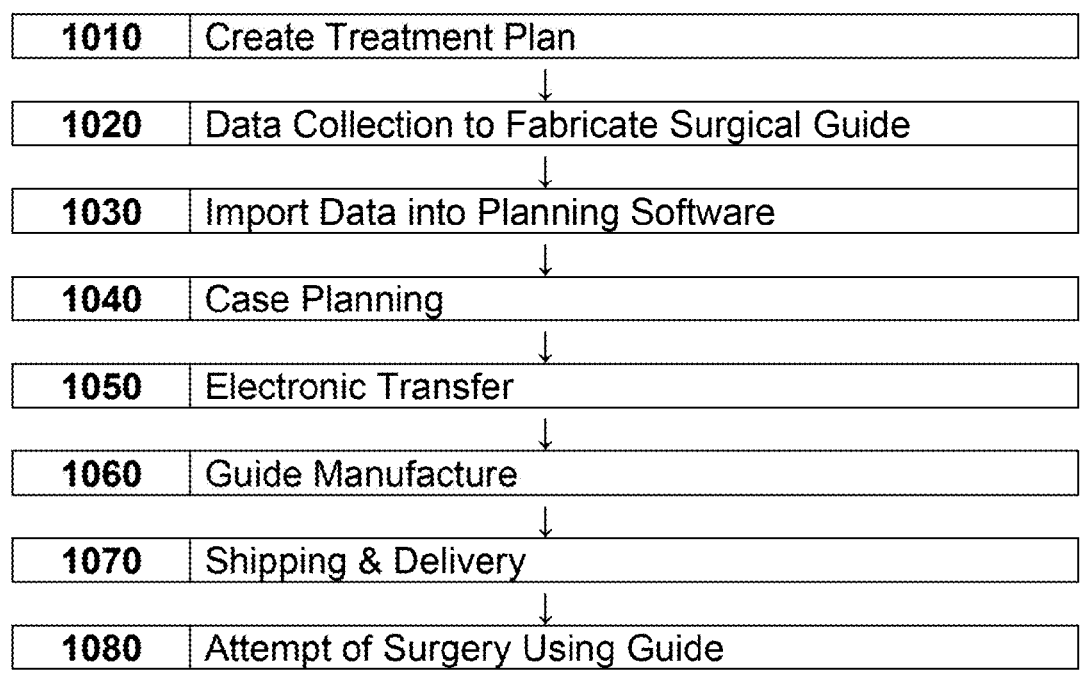
FIG. 1 is a flowchart of the prior art process for preparing a bore to receive a dental implant.

The drill trajectory should allow for the final bore to be created with a desirable tolerance between the surface of the drilled bore and the edge of the jaw bone towards the inside of the mouth (lingual/palatal side), the edge of the jaw bone towards the outside of the mouth (facial, or buccal-towards cheeks, sometimes labial-towards lips). The drill trajectory should allow for the final bore to be created with a desirable tolerance between the surface of the drilled bore and the adjacent teeth (mesial and distal). The drill trajectory should allow for the final bore to be created with a desirable tolerance between the surface of the drilled bore and the apical end of the jawbone.

Different dentists may have different preferences for how they choose a drill trajectory based upon the patient anatomy. A set of rules for determining a drill trajectory based on patient anatomy may be called a drill trajectory protocol or implant protocol. One implant protocol may focus on a different set of landmarks on the patient anatomy than a set of landmarks used for a different implant protocol.

The present disclosure does not address the specific advantages or disadvantages of any of the known implant protocols or suggest new protocols. The present disclosure may be used with any implant protocol and set of patient anatomy landmarks used by that protocol.

Using the implant protocol and a three-dimensional model, a restorative trajectory is obtained. For purposes of this disclosure and the claims based upon this disclosure, a restorative trajectory is the three-dimensional position, angle, and height for implant placement determined by the anatomical needs for restoring form and function with no regard to the available anatomical structures for osseointegration of the implant. The implant has a purpose of providing an anchor for a prosthetic device. The restorative trajectory has a focus on positioning the prosthetic device so that the prosthetic device is ideally placed relative to other teeth and landmarks to provide the desired traits with respect to chewing, appearance, and other characteristics known in the dental arts. In other words, a restorative trajectory is the three-dimensional position, angle, and height for implant placement determined by the anatomical needs for restoring form and function with no regard to the available anatomical structures for osseointegration of the implant. The implant has a purpose of providing an anchor for a prosthetic device. The restorative trajectory has a focus on positioning the prosthetic device so that the prosthetic device is ideally placed relative to other teeth and landmarks to provide the desired traits with respect to chewing, appearance, and other characteristics known in the dental arts. Examples of items not relevant to the restorative trajectory include desired measurement for platform height to bone crest;
  minimum distance between edge of implant and apical edge of bone available for implant (given that implants may be oriented upward in the maxillary (upper) jaw or downward in the mandibular (lower) jaw, the terms apical and coronal or (occlusal/incisal) are used instead of inferior/superior or cephalad/caudal).
  minimum distance between edge of implant and mesial edge of bone available for implant;
  minimum distance between edge of implant and distal edge of bone available for implant; and
  minimum distance between the edge of the implant and outer edge of the bone;
  minimum distance between the edge of the implant and the inner edge of the bone.

Thus, the term restorative trajectory is distinct from the implant trajectory discussed above in connection with prior art practices as the restorative trajectory does not make adjustments or compromises based upon the bone volume of the patient in the relevant portion of the jawbone nor proximity to anatomic structures to be avoided during drilling. A second trajectory, the surgical trajectory makes those adjustments later in the process as discussed below.

Once an implant protocol is selected, surface anatomical landmarks are input into the software. First a three-dimensional image of the relevant set of teeth or relevant edentulous dental ridge contours is needed to be input into the system. The input file made from one of many different imaging devices used by dentists to get an image of a patient's teeth. One known method is to take an impression of the teeth and dental arch and use this impression to make an accurate model of the patient's mouth. This model may be scanned with an extraoral optical scanner to obtain a digital file that captures the three-dimensional model. Alternatively, an optical scanner may be placed inside the patient's mouth to obtain a three-dimensional model without taking impressions and making a physical model. Another scanning device is CBCT (cone beam computed tomography). Other imaging devices may be used to provide the three-dimensional image information.

Once the data is within the software, the three-dimensional model may be annotated with landmarks such as central fossa points on a series of relevant teeth so that a central fossa line may be created for use by the implant protocol. Other landmarks may include the occlusal plane, facial axial angles of adjacent teeth, mesial tooth transverse angle, mesial contact, distal tooth transverse angle, distal tooth contact, CEJ/free gingival margin, restorative outline, and a desired frame beginning point and end point. (Frame discussed in more detail below). The full range of landmarks that may be noted on the three-dimensional model and the use of the landmarks in various implant protocols are beyond the scope of the present disclosure. The teachings of the present disclosure may be used independent of the particular implant protocol and landmark set used to create the restorative trajectory.

Creating a Frame and a Cartridge Based Upon the Restorative Trajectory.

Through use of a selected implant protocol, three-dimensional model of the surface of various structures, and landmarks that have been identified, a restorative trajectory is created. Software may allow the dentist to manually tweak the restorative trajectory based upon experience and preferences. However, a restorative trajectory is eventually chosen.

Figure 2:
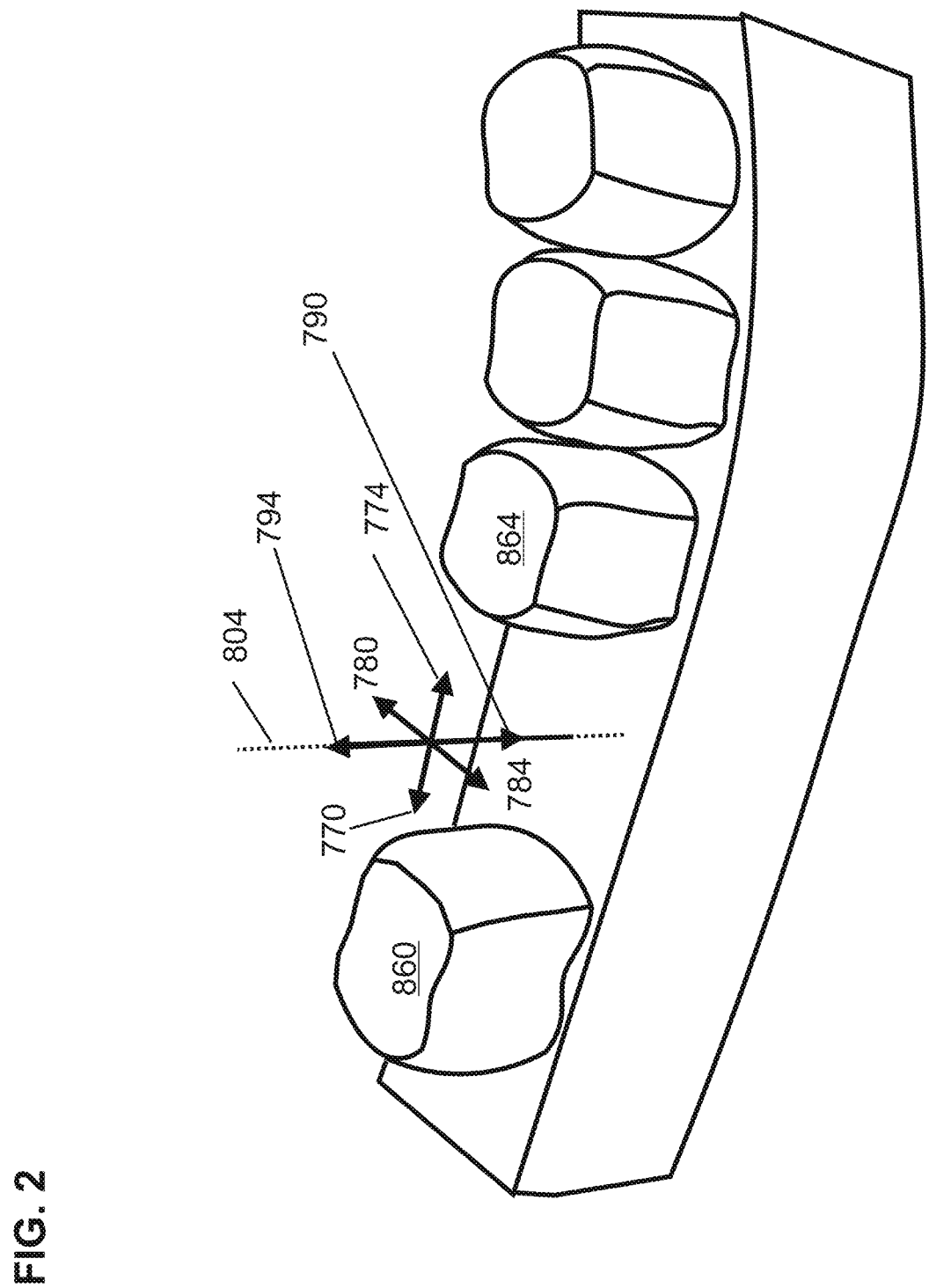
FIG. 2 shows a model of the relevant portion of a patient's mouth.

FIG. 2 shows a model 800 of the relevant portion of a patient's mouth. The model 800 includes a restorative trajectory 804 for the drilling to place the implant (not shown) into the jaw of the patient in such a way as to optimize the implant location for allowing a prosthetic tooth to be placed upon the top of the implant and act effectively in mastication and be aesthetically pleasing. Note that dentists use a modified Cartesian coordinate system where:

the X axis is aligned with distal-mesial axis with mesial positive;
  the Y axis is aligned with the inner-outer axis with outer positive; and
  the Z axis is aligned with the apical-coronal axis with coronal positive.

As the distal-mesial axis is taken relative to set of teeth on a curve, it is convenient to define the distal-mesial axis then define the inner-outer axis perpendicular to the distal-mesial axis.

In FIG. 2, the directions are provided as
  Distal 770;
  Mesial 774;
  Inner 780;
  Outer 784;
  Apical 790; and
  Coronal 794.

Figure 3:
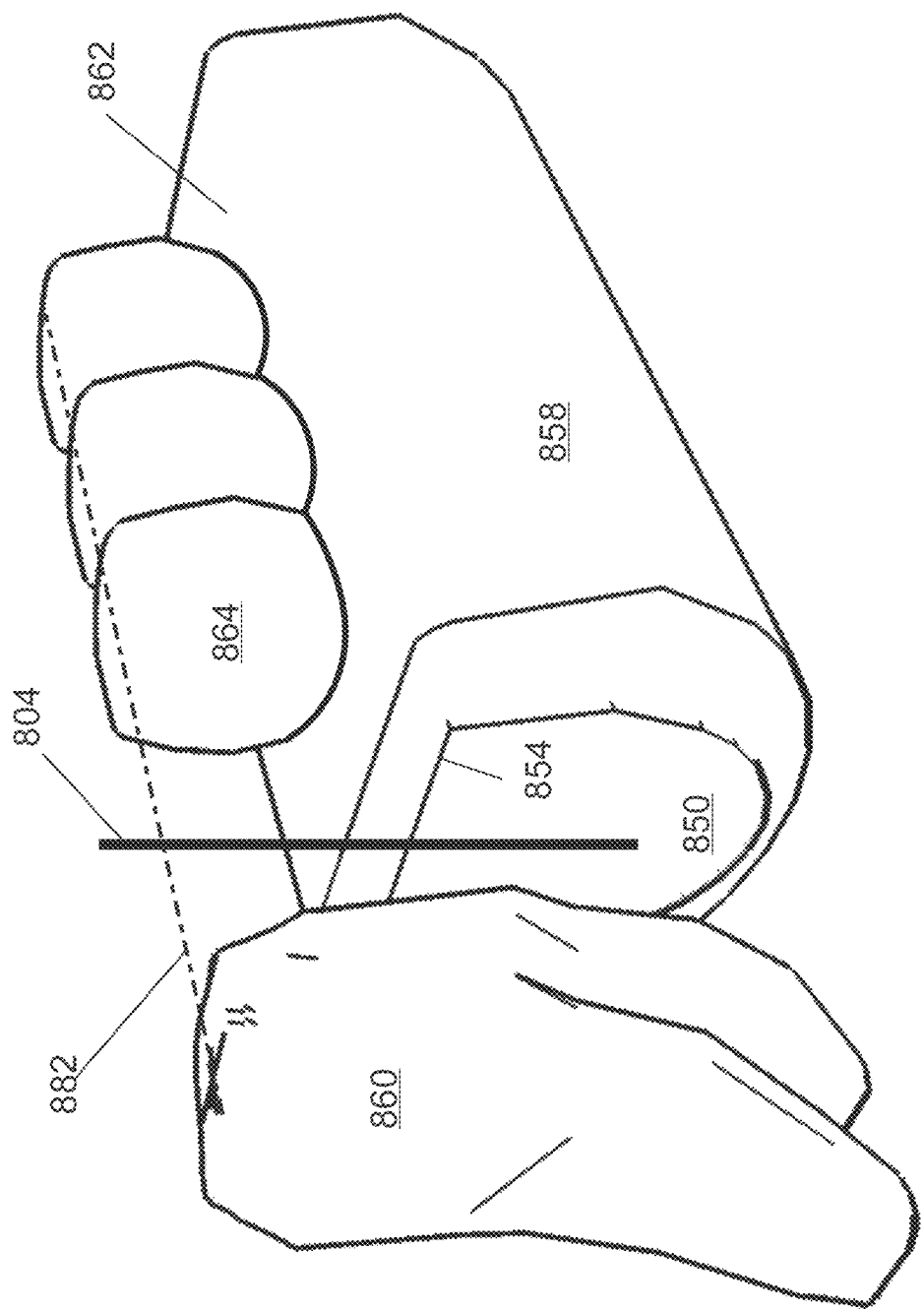
FIG. 3 shows a cross-section taken on the inner-outer by apical-coronal plane revealing the bone volume at the plane of interest.

FIG. 3 shows a cross-section taken on the inner-outer by apical-coronal plane revealing the bone volume 850 at the plane of interest, the bone crest 854, the surface of the soft tissue 858 and the occlusal plane 882. The bone crest 854, soft tissue surface 862, and occlusal plane 882 are important for setting the implant height and planning for the prosthetic tooth. The bone volume 850 is not relevant to the restorative trajectory 804 but will become relevant when preparing for the surgical trajectory.

Cartridge Planning.

A cartridge will hold the various guide sleeves used in the process. A standard size cartridge may be used (possibly one of several nominal sized cartridges) or a custom sized cartridge may be made for the surgical situation.

Figure 4:
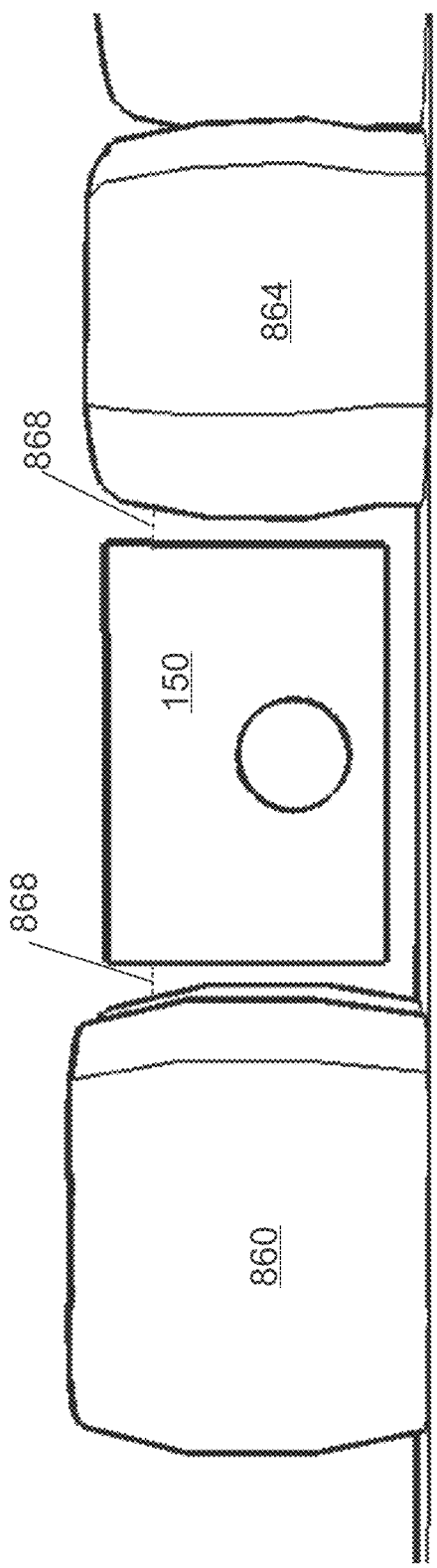
FIG. 4 shows a planning process for a cartridge reflecting the restorative trajectory.

FIG. 4 shows a planning process for a cartridge 150 for the restorative trajectory 804. The height of the cartridge (apical-coronal) may be chosen so that when the cartridge 150 is fit within the surgical frame, the cartridge 150 does not extend in the coronal direction excessively such that it is in the way. The length of the cartridge 150 in the distal-mesial direction may be determined by the distance between the adjacent distal tooth 860 and the adjacent mesial tooth 864 and desired offsets 868.

Figure 5:
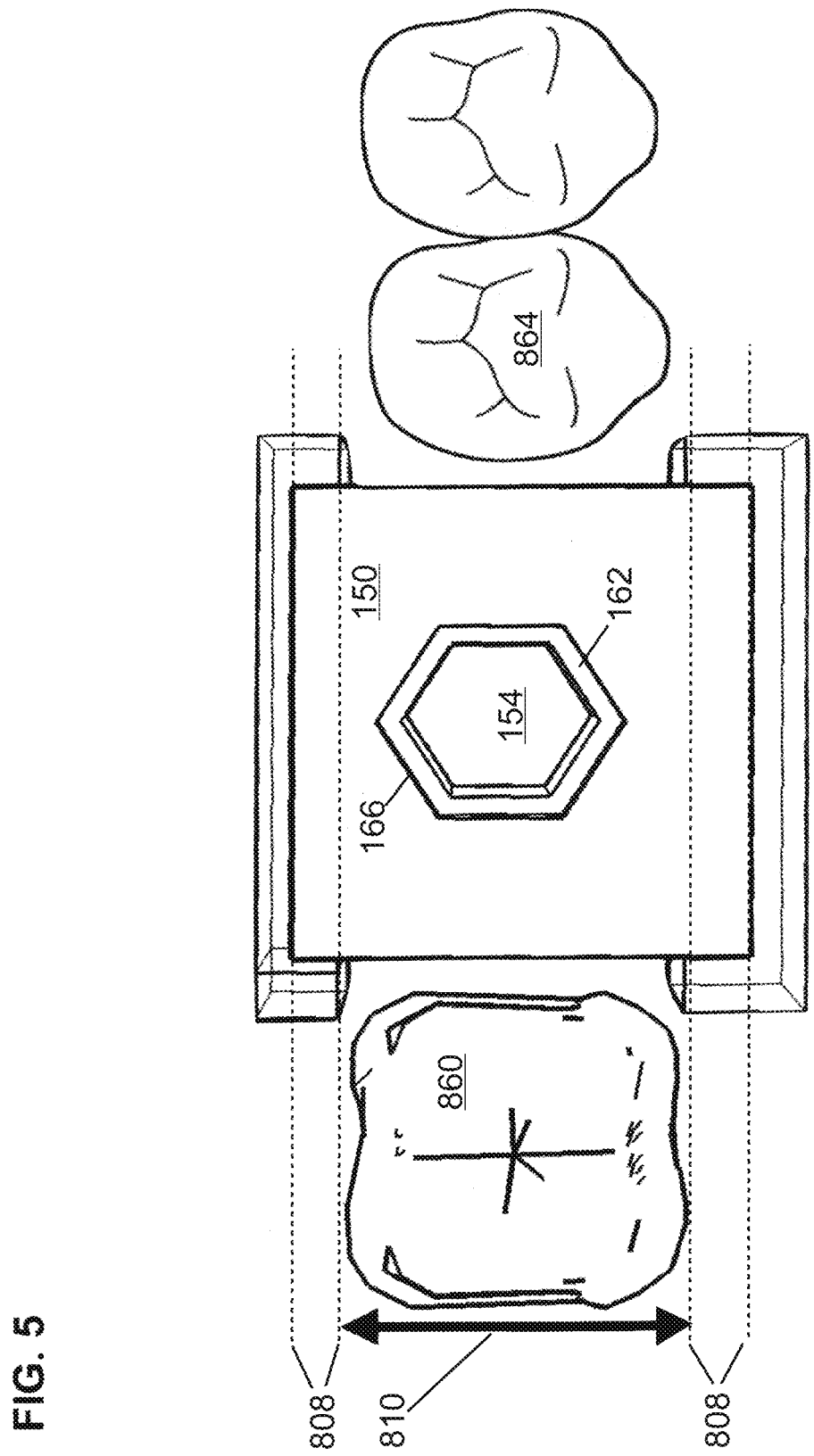
FIG. 5 shows a planning process for the width (inner-outer) of the cartridge.

FIG. 5 shows a planning process for the width (inner-outer) of the cartridge 150. The width may be set to be the combination of the inner-outer measurement 810 for the tooth with the largest inner-outer measurement plus the additional amounts 808 desired to interact with the surgical frame.

The planned cartridge 150 may be adjusted to have tapers so that the apical end of the cartridge 150 has a reduced distal-mesial dimension and a reduced inner-outer dimension than at the coronal face of the cartridge. The design for the chamber 108 (discussed below) in the frame 104 (discussed below) to receive the cartridge 150 would be sized for a snug fit but allow the cartridge 150 to be removed so that another cartridge with a revised trajectory could be inserted in the frame in the same position. Those of skill in the art will appreciate that other shapes may be used to help retain the cartridge in the frame such an appropriate form of dovetail.

Instead of sending data files to create a monolithic surgical guide with integrated bore to use as the outermost guide sleeve, a multi-piece surgical guide with a frame and a removable cartridge that can receive the guide sleeve is manufactured in accordance with the restorative trajectory from the planning process.

The cartridge 150 and frame 104 may be created at the dental facility using one of the known processes for additive manufacturing. One such additive manufacturing process is 3D printing although one of skill in the art would be able to use one or more of the many processes in additive manufacturing to convert appropriate data files for the frame and cartridge into three-dimensional objects. The additive material process and material used will need to be selected to accommodate the need for the frame to correspond to the shapes of teeth in the patient's mouth (for non-edentulous procedures). Creating a form that corresponds to the shape of teeth presents challenges in the slopes required to mirror the shape of teeth. Another complication is that the tooth may narrow from a largest cross section to a smaller cross-section near the coronal edge of the soft tissue. Thus, the material for the frame may need to be able to flex in order to be inserted over the larger cross section and engage the smaller cross section. One of skill in the art will appreciate that some implant procedures occur with edentulous areas adjacent to the surgical site and the frame 104 will conform to the soft tissue 858 present.

One can appreciate that creating a frame 104 and a cartridge 150 using an additive manufacturing process avoids having a patient sit with impression compound in the mouth while the impression compound is first worked into position and then allowed to harden sufficiently for subsequent process steps.

Figure 6:
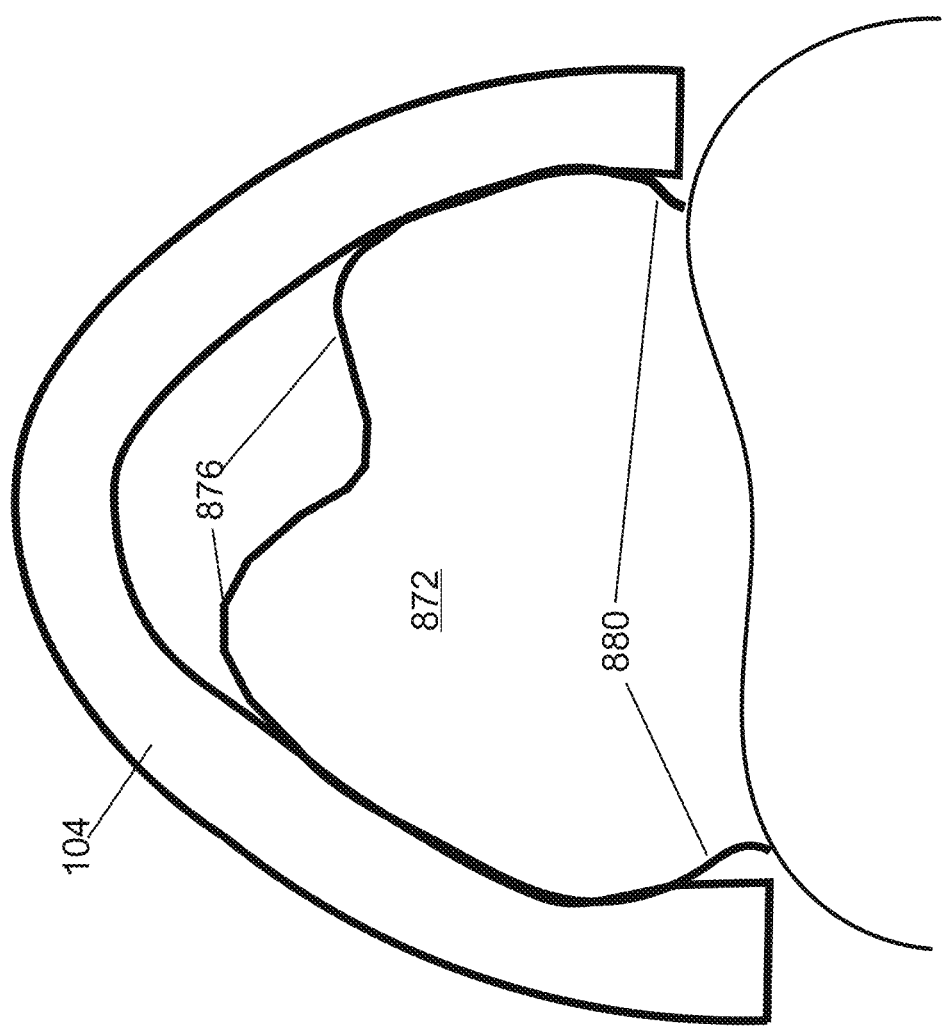
FIG. 6 shows a proposed frame interacting with a tooth.

As shown in FIG. 6, the proposed frame 104 does not need to accurately trace all of the tooth surfaces in order to achieve the task of firmly placing the cartridge 150 (not shown here) in the proposed position over the surgical site. Some portions of the tooth 872 may not be in contact with the frame 104. Portions 876 of tooth 872 are not in contact with the frame 104 because of limitations from the additive manufacturing process in changing slope. Portions 880 of tooth 872 are not in contact with the frame 104 as the frame material is not sufficient flexible to reach the undercut. However, the frame 104 need only adequately fit the relevant tooth 872, not necessarily fit the tooth 872 perfectly.

Figure 7:
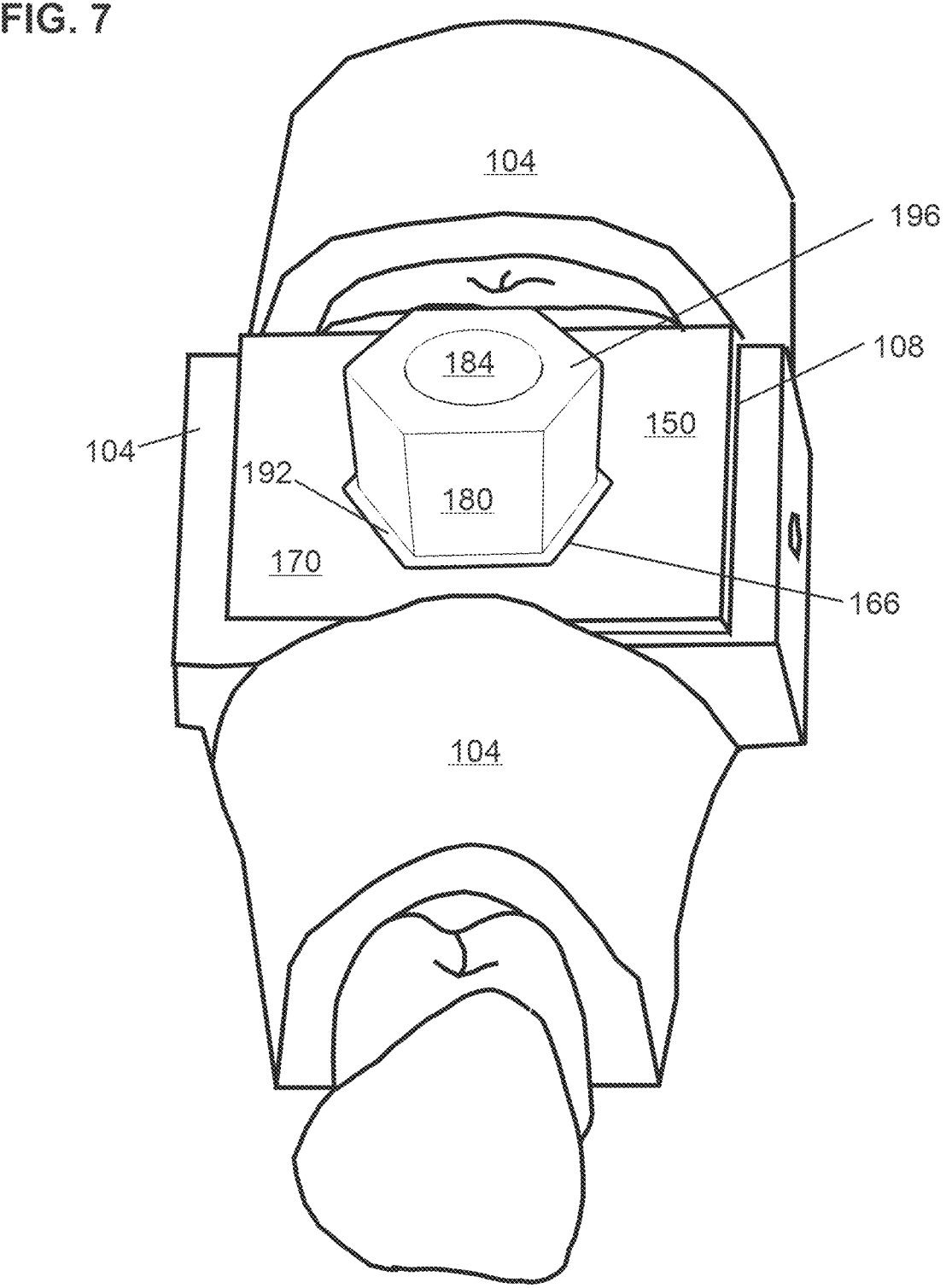
FIG. 7 shows a frame with chamber to receive removable cartridge.

FIG. 7 shows a frame 104 with chamber 108 to receive removable cartridge 150. The chamber 108 may have an apical-coronal depth that is less than the apical-coronal depth of the cartridge 150 so that the cartridge 150 extends beyond the coronal edge of the frame 104. Extending the cartridge 150 above the coronal edge of the frame 104 facilitates removal of the cartridge 150 from the frame 104. Removable cartridge 150 has an opening 154 (not visible here as the guide sleeve 180 is present) for receipt of a guide sleeve 180. Guide sleeve 180 has a bore 184 running from the coronal face 196 to the apical face 194 (not visible here) to allow an instrument to reach the soft tissue and the jawbone beyond.

The opening 154 in the cartridge 150 may be symmetric as with the hexagonal shaped opening 154. Through bore 184 in the guide sleeve 180 is aligned to be perpendicular from the apical face 194 and coronal face 196 of the guide sleeve 180. The bore 184 is located in the middle of the guide sleeve 180. Thus, rotation of the guide sleeve 180 within the opening 154 of the cartridge 150 is irrelevant as the trajectory of the drill into the jawbone is controlled by the position and angulation of the opening 154 in the cartridge 150. The insertion depth of the guide sleeve 180 is precisely controlled by a stop flange 192 that engages with a stop flange plane 162 (not shown here) and a stop flange perimeter 166 that surrounds the stop flange 192. Ideally the cartridge 150 has a recessed stop flange plane 162 to receive the stop flange 192 at a sufficient depth so that a coronal side of the stop flange 192 is flush with the coronal face 170 of the cartridge 150

As the guide sleeve 180 has a bore 184 through the midline of the guide sleeve 180, the guide sleeve 180 may be a reusable part made from a material that allows for machining close tolerances for the stop flange 192, bore 184, and other dimensions. If the guide sleeve 180 is to be used with different patients, the guide sleeve 180 will need to tolerate at least one sterilization process known in the dental arts. Surgical stainless steel is one suitable material for the guide sleeve.

Use of the Restorative Cartridge.

Now that the restorative trajectory 804 is placed over the surgical site via the precise placement of the bore 184 in the guide sleeve 180 placed in the cartridge 150 in frame 104. Detailed measurements and other inputs can be obtained to help plan the surgical trajectory which takes into account anatomic issues that influence the desired positioning of the implant.

Crest of Bone and Soft Tissue Depth.

Figure 8:
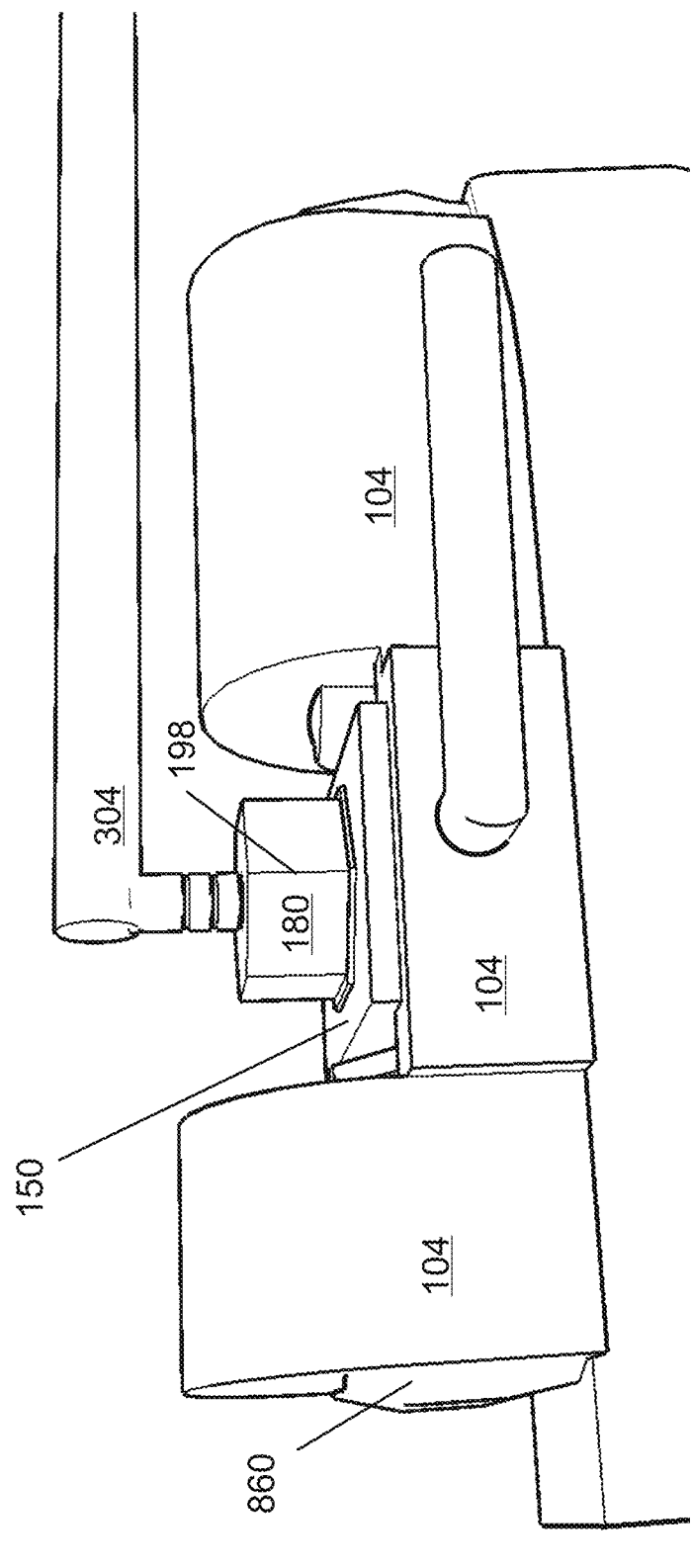
FIG. 8 is an outer-mesial perspective view showing the use of a probe.
Figure 9:
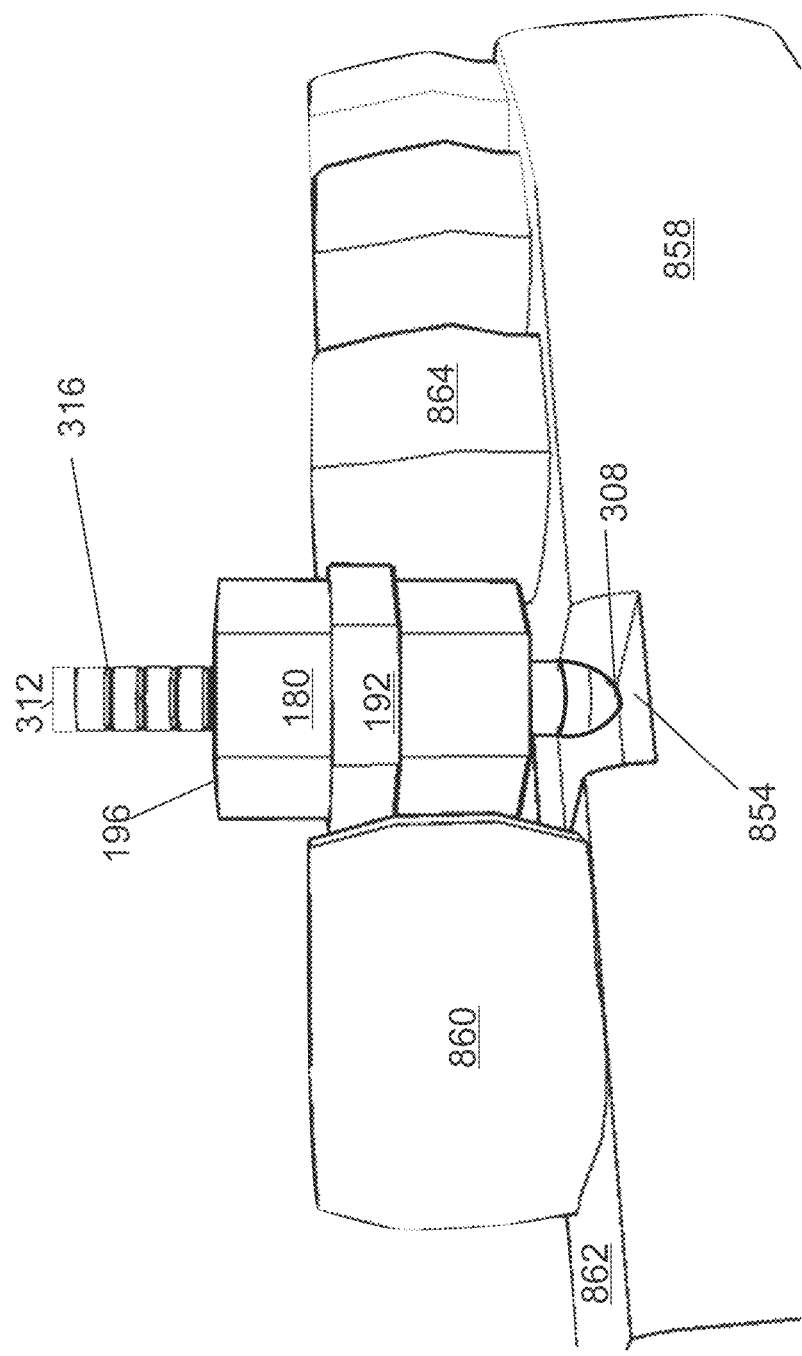
FIG. 9 is another outer-mesial perspective view of the components from FIG. 8 but with the frame and the cartridge rendered invisible so as to allow for viewing of the inserted probe tip.

FIG. 8 and FIG. 9 show two views of a probe 304 with a narrowed probe tip 308 and probe outer diameter 312 which fits snuggly within the bore 184 of the guide sleeve 180 so that the probe 304 strikes the soft tissue surface 862 and penetrates to the bone crest 854. The insertion depth of the probe 304 as the probe tip 308 rests on the bone crest 854 may be discerned by markings 316 placed on the probe 304. Assessing depth with a level of accuracy of $\frac{1}{5}^{th}$ of a millimeter is more than sufficient for this process. The markings 316 can be translated to provide a distance between the probe tip 308 and the coronal face 196 of the guide sleeve 180. With the frame 104 shown here has an open distal end as the frame straddles the adjacent distal tooth 860, some frames 104 may have a closed end if the distal or mesial end of the frame 104 is in a location without a tooth to straddle.

FIG. 9 is shown with the frame 104 and the cartridge 150 rendered invisible so as to allow for viewing of the inserted probe tip 308 passing through the layer of soft tissue 858 to reach the bone crest 854.

Determining Depth of Soft Tissue.

Once the distance from the coronal face 196 of the guide sleeve 180 to the bone crest is determined, the probe 304, guide sleeve 180 and cartridge 150 may be removed to expose a probe bore 886 in the soft tissue 858. The depth of soft tissue 858 may be measured by placing a washer (not shown here) on probe 304 near the probe tip 308 and inserting the probe to the bone crest 854. The washer will be forced to move in a coronal direction on the probe 304. The distance of the washer from the probe tip 308 can be measured after the probe is removed from the mouth to provide a measurement of the depth of the soft tissue 858.

Two-Dimensional X-Ray.

An X-ray of the surgical site along with radiographic opaque markers on the inserted components is helpful for planning the surgical trajectory. A preferred process is to use an alignment system 400 for the X-ray that is aligned with the restorative trajectory.

Figure 10:
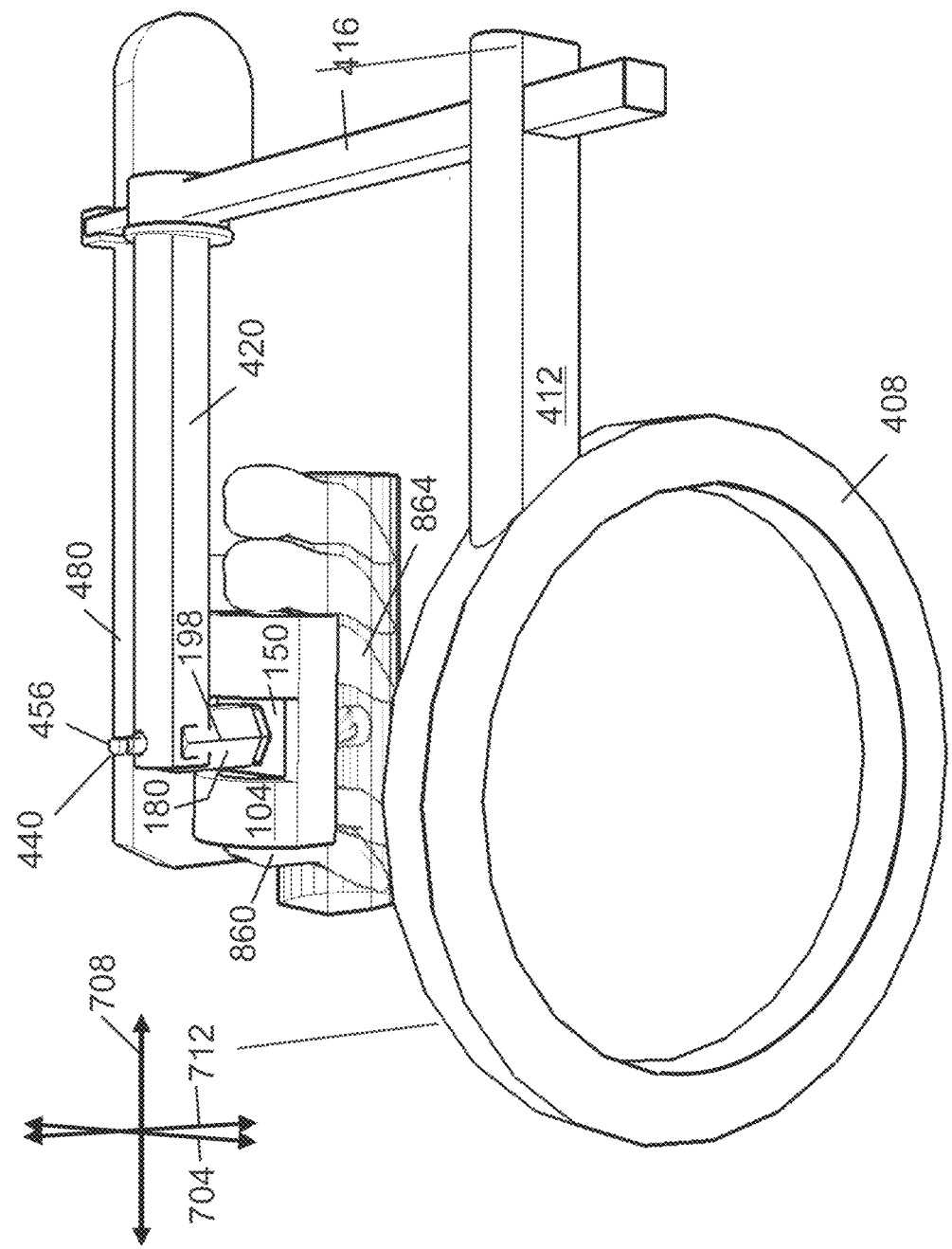
FIG. 10 shows a guide ring which orients the X-ray source and the components that orient the guide ring.

FIG. 10 shows a guide ring 408 which orients the X-ray source (not shown here). For the convenience of the viewer, a set of axes (704, 708, and 712) is presented in FIG. 10 as the guide ring 408 is aligned relative to these axes. The set of axes has been moved away from the restorative trajectory 804 to avoid undue clutter but the axes are all defined based upon the restorative trajectory 804 (not shown here but aligned with the centerline of the drill bit 440). The guide ring 408 aligns the X-ray source 404 along the inner-outer axis 704 with respect to the surgical site and perpendicular to a plane defined by the apical-coronal axis 712 for the restorative trajectory and the distal-mesial axis 708. Thus, the X-ray source 404 (not shown here) is aligned with the outer hex ridge 198 which is itself aligned by the alignment of the opening 154 (See FIG. 8) of the cartridge 150 to be aligned with the plane defined by the inner-outer axis 704 and the apical-coronal axis 712 for the restorative trajectory.

The guide ring 408 has a guide ring arm 412 to offset the guide ring 408 from a spacer arm 416. The spacer arm 416 is connected to an egress arm 420 which carries the orientation alignment out of the mouth of the patient for use by the spacer arm 416 and guide ring arm 412. A centerline of the egress arm 420 is perpendicular to the plane defined by the inner-outer axis 704 and the apical-coronal axis 712 for the restorative trajectory.

Figure 11:
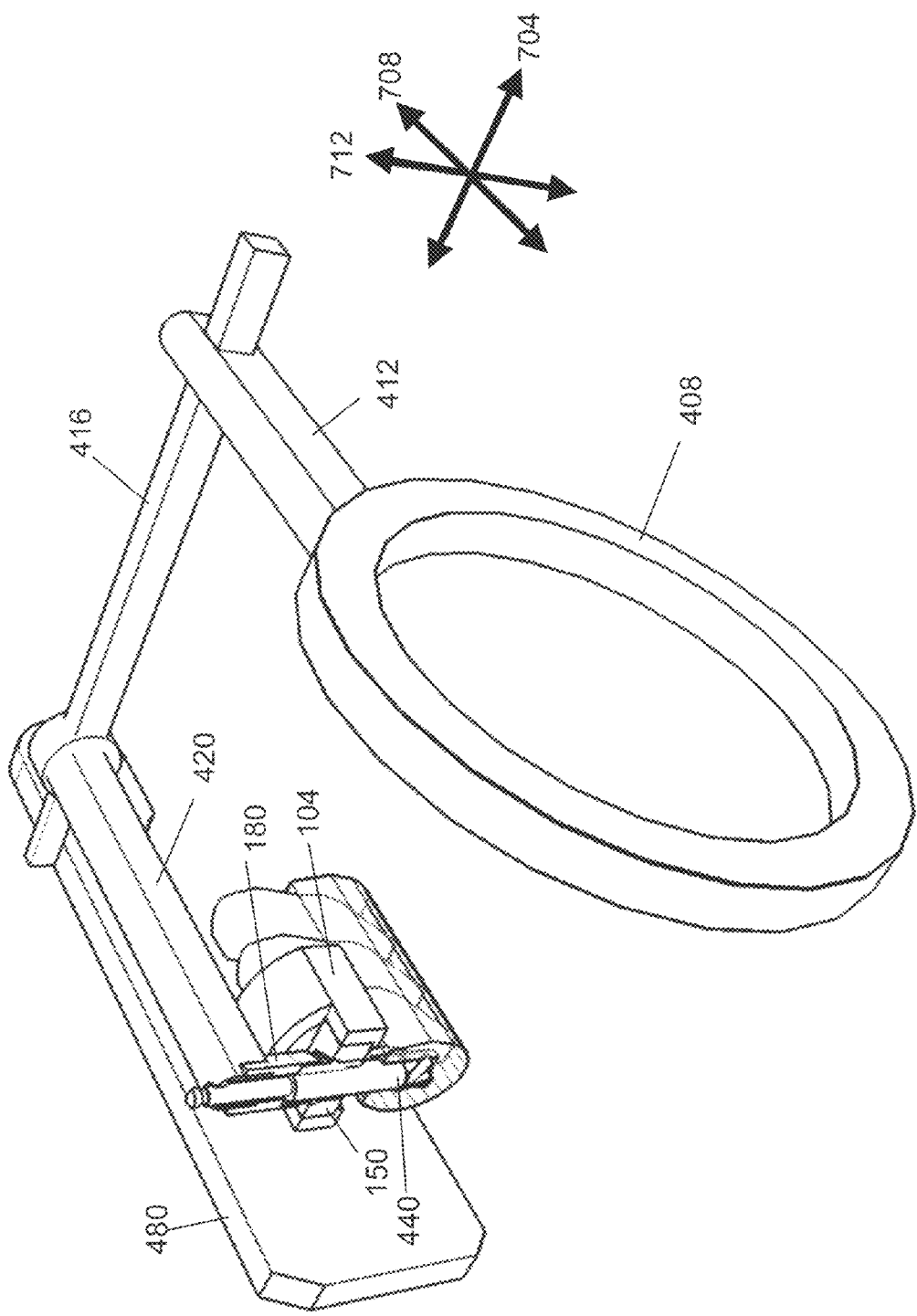
FIG. 11 shows a top perspective view of FIG. 10 with a partial cross section in the inner-outer by apical-coronal plane.

An astute observer will note that figures FIG. 10 and FIG. 11 lack the optional irrigation bores discussed elsewhere as the emphasis is on other features in the drawings.

FIG. 11 shows a top perspective view of FIG. 10 with a partial cross section in the inner-outer 704 by apical-coronal 712 plane. Visible in FIG. 11 are guide ring 408, guide ring arm 412, spacer arm 416, egress arm 420, a portion of guide sleeve 180, a portion of cartridge 150, and a portion of frame 104. Also visible is drill bit 440.

The inner-outer axis 704, distal-mesial axis 708, and apical-coronal axis 712 are viewable in this perspective view. Sensor holder 480 is shown to show the inline placement of the sensor holder 480 with the guide ring 408. Note that the sensor holder 480 is positioned parallel to the guide ring 408, and guide ring arm 412. The mechanism that holds the sensor holder 480 is not shown in FIG. 11 but will be discussed below.

Figure 12:
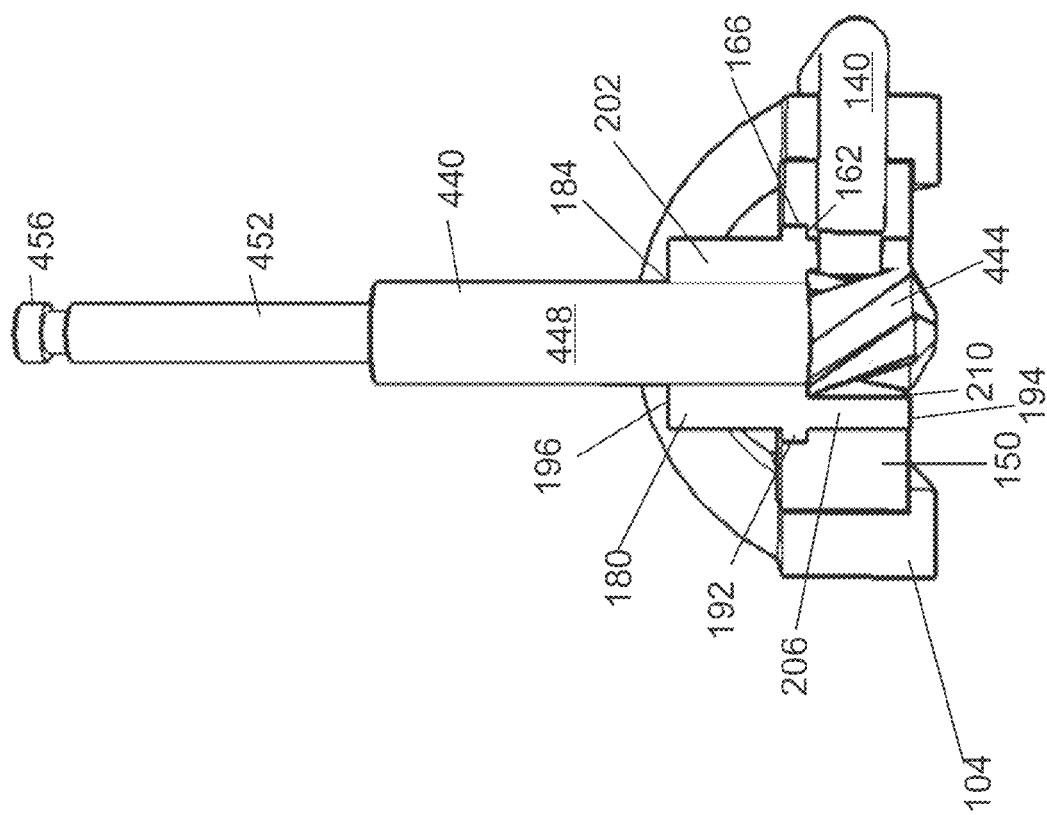
FIG. 12 shows a partial cross section of a frame, cartridge, and guide sleeve in the inner-outer by apical-coronal plane.

FIG. 12 shows a partial cross section of a frame 104, cartridge 150, and guide sleeve 180 in the inner-outer 704 by apical-coronal 712 plane. The drill bit 440 is not shown in cross section. The drill bit 440 has distal cutting section 444. The maximum width of the distal cutting section 444 is wider than the width of the intermediate section 448. The intermediate section 448 is constrained by the bore 184 as it passes through the coronal section 202 of the guide sleeve 180. This constraint between coronal section 202 and the intermediate section 448 maintains the trajectory of the distal cutting section 444. An expanded bore 210 in apical section 206 is sized to receive the distal cutting section 444 of the drill bit 440 so that after the drive engagement section 456 is inserted from the apical face 194 through the coronal face 196 through the bore 184 in the guide sleeve 180, a user may grasp the upper shank 452 or the drive engagement section 456 to carry a guide sleeve 180 to and from the surgical site. The intermediate section 448 and upper shank 452 may be marked with indicia (not shown here) to allow for depth of insertion measurements to be made. FIG. 12 has the optional irrigation ports discussed below. The upper shank 452 and drive engagement section 456 would typically be inserted into a corresponding opening in a drill (sometimes called a surgical hand piece) before drilling.

FIG. 12 also shows the stop flange plane 162 surrounded by the stop flange perimeter 166.

One of skill in the art will recognize that the coronal end of the expanded bore 210 may be placed coronal or apical relative to the stop flange 192 depending on the overall apical-coronal length of the guide sleeve 180, and the tradeoffs in providing more guidance to the drill bit shank versus a need to retract an longer distal cutting section 444.

Figure 13:
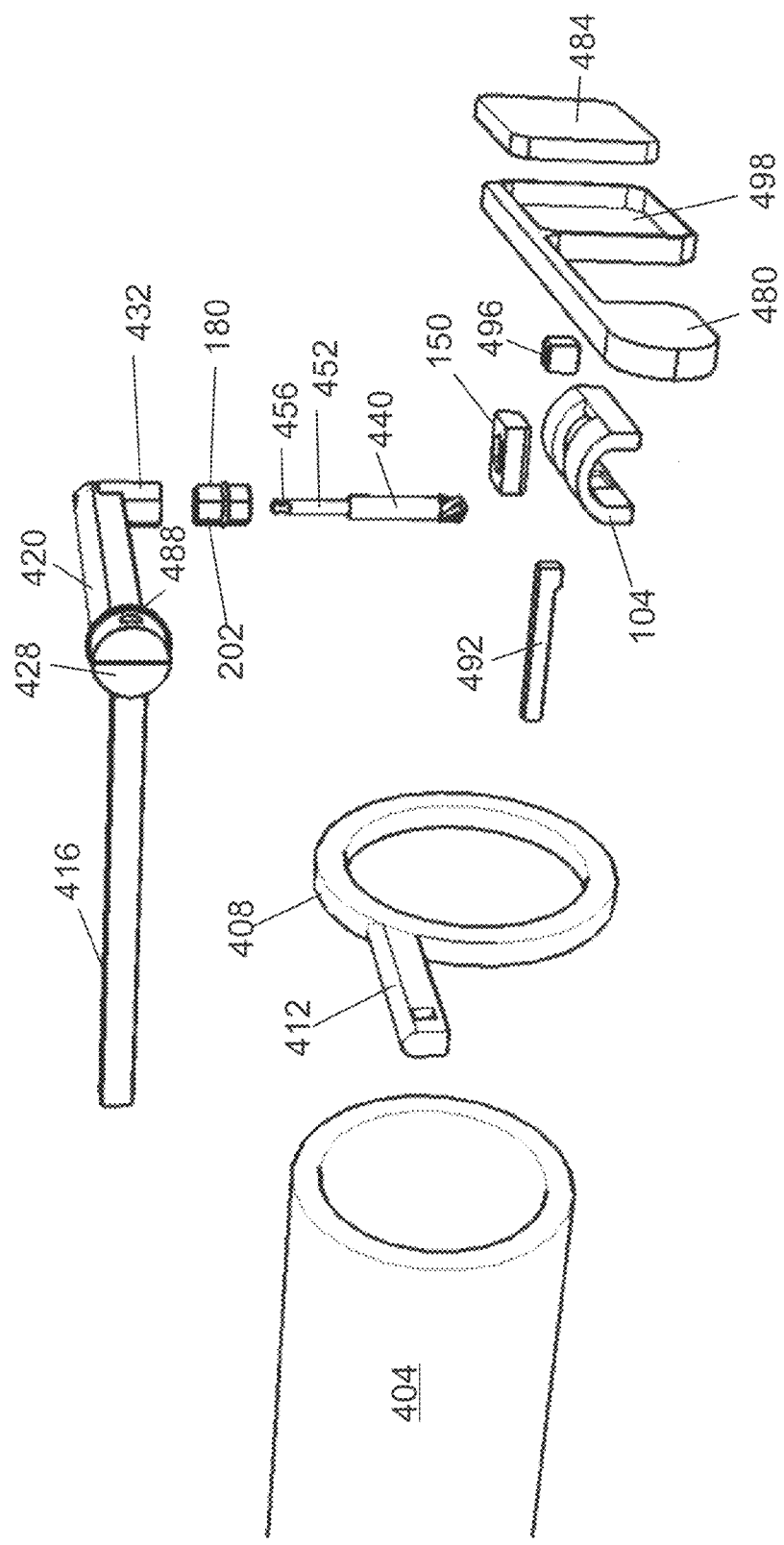
FIG. 13 shows an exploded diagram to explain the positioning of sensor holder relative to the guide sleeve.

FIG. 13 shows an exploded diagram to explain the positioning of sensor holder 480 relative to the guide sleeve 180. As previously discussed, the X-ray source 404 is aligned with guide ring 408 by an engagement of the guide ring arm 412 with the spacer arm 416 so as to put the guide ring 408 perpendicular to the spacer arm 416. The spacer arm 416 engages with a first cavity 424 (not shown here) in bidirectional hub 428 on an external end of egress arm 420. At the distal end of the egress arm 420, a female hex sleeve 432 engages the coronal section 202 of the guide sleeve 180. As the cartridge 150 was created to align the guide sleeve 180 with the geometry of the surgical site, the geometry of the surgical site is captured by the female hex sleeve 432 so that through a series of perpendicular connections, other components can be aligned with the surgical site.

In the present example, a symmetric hexagonal shape is used for the guide sleeve 180 with an outer hex ridge 198 (not shown here) on the outer side of the surgical site but indicating the inner-outer axis 704. One of skill in the art will appreciate that the guide sleeve 180 could have a flat face of the hexagonal shape facing the outer direction and hex ridges on the distal-mesial axis 708 as long as the egress arm 420 and female hex sleeve 432 were adjusted appropriately.

The female hex sleeve 432 may be sized to allow the female hex sleeve 432 to fit over the drive engagement section 456 and the upper shank 452 of the drill bit 440.

The sensor holder 480 holds the X-ray sensor 484 in a sensor cavity 498. The sensor holder 480 is positioned by a sensor spacer 492 that engages a second cavity 488 in bidirectional hub 428 and engages a spacer receptacle 496 on the sensor holder 480.

The bidirectional hub 428 may be rotated 180 degrees to place the sensor holder 480 to the left of the bidirectional hub 428 and the guide ring 408 to the right of the bidirectional hub 428 so that all quadrants of the mouth may be used with the X-ray alignment system 400. An alternative would be to have a bidirectional hub 428 that did not rotate but had a first cavity 424 that matches the second cavity 488 so that either cavity could receive either the spacer arm 416 or the sensor spacer 492.

An X-ray taken with the X-ray source 404 aligned with the guide ring 408 will provide X-rays to the X-ray sensor 484 in a known relationship with the surgical site. After the digital data from the X-ray sensor 484 is within the procedure planning program auto-calibration with the known shape and position of the guide sleeve 180 sets the three axes:

zero on the apical-coronal axis 712 is set to the coronal face 196 of the guide sleeve 180;

zero on the inner-outer axis 704 is on the restorative trajectory; and zero on the distal-mesial axis 708 is on the restorative trajectory and aligned with the outer hex ridge 198.

With the guide sleeve 180 as a landmark, other biological landmarks may be identified automatically or manually on the X-ray results. The biological landmarks may include bone crests 854. The distance from the coronal face 196 of the guide sleeve 180 may be compared with the probe depth to the coronal face 196 of the guide sleeve 180 when a probe was inserted through the bore 184 in the guide sleeve 180 through the soft tissue 858 to the bone crest 854. The bone crest 854 indications available from the X-ray data include bone crest 854 indications for the entire distal-mesial range.

From this information, the implant may be planned to have a coronal face at a desired distance from at least one biological landmark such as bone crest 854, soft tissue surface 862, CEJ (cementoenamel junction), or contact. In this context, contact is where the anatomical crown meets the anatomical root. The planning process could align the coronal face 754 (shown below) of the implant with any other biological landmark of relevance to the implant planning protocol. For example the coronal face 754 of the implant 750 can be planned to be placed zero millimeters above the bone crest 854.

The nearby roots of adjacent teeth may be identified automatically or manually.

The apical edge of the bone volume may be identified automatically or manually. A safety zone may be used to ensure the planned surgical trajectory stays safely clear of the apical edge of the bone volume. For example if the total length of bone in the apical-coronal direction is 11 millimeters and a 2 millimeter safety edge is desired then the depth of available bone is 9 millimeters.

Figure 14:
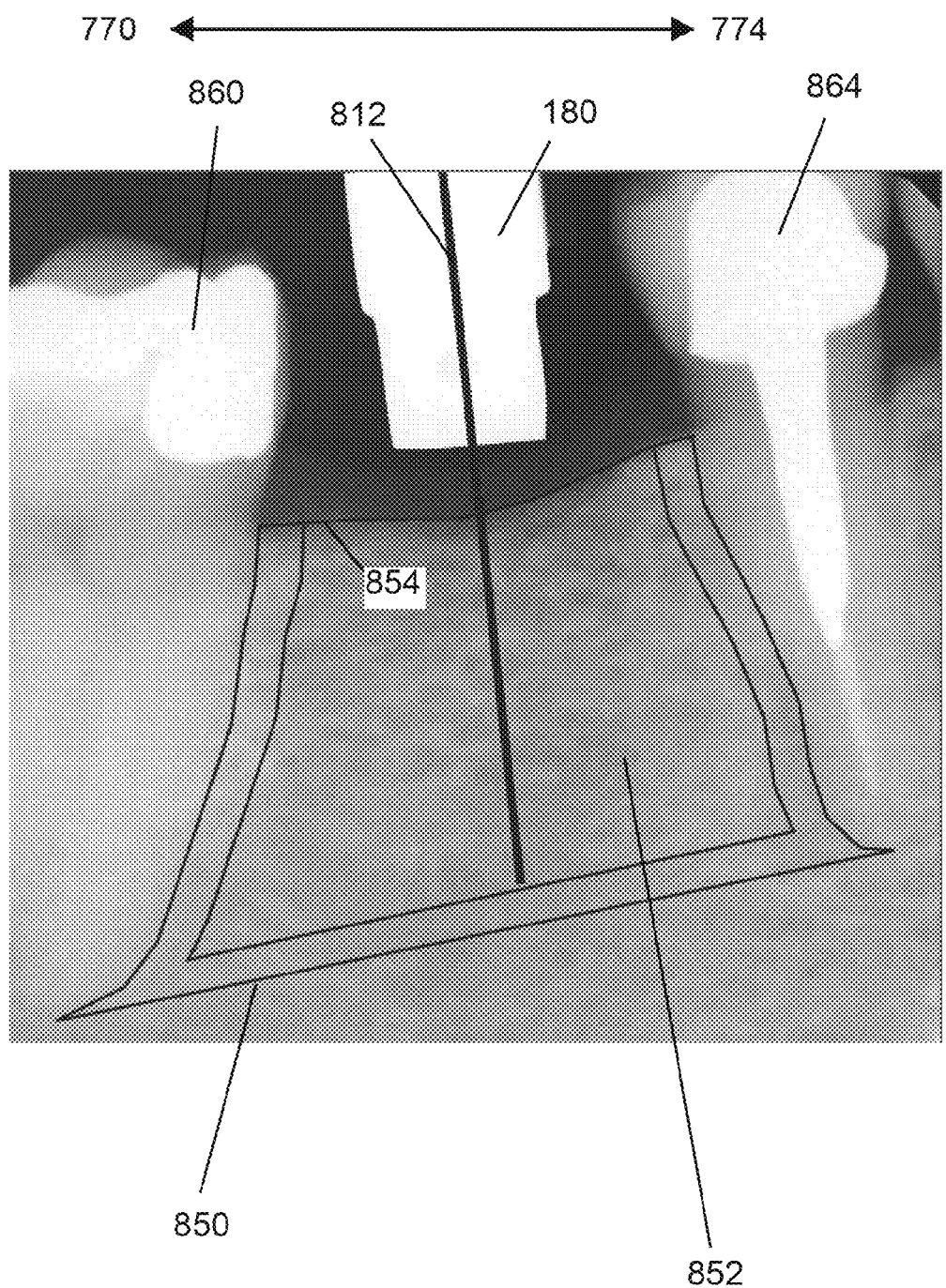
FIG. 14 shows part of the planning process where an intermediate trajectory for a proposed implant.

FIG. 14 shows part of the planning process where an intermediate trajectory 812 for a proposed implant 750. As there is a process to modify the restorative trajectory 804 to become the surgical trajectory 814, during the process there may be trajectory iterations which we can call intermediate trajectory 812. The trajectory 812 is shown within the safe bone volume 852 which is set off by safety margins from total bone volume 850. The safety margin on the distal side 770 may be different than the safety margin on the mesial side 774. The implant length is selected to not extend beyond the safe bone volume 852 from the bone crest 854. Many other relationships between the implant and anatomic features may help shape the surgical trajectory 814. The restorative trajectory 804 may be modified based upon the input from the two-dimensional X-ray to make adjustments in location and angulation in the distal-mesial 708 by apical-coronal 712 plane. Some of these relationships are part of specific planning protocols or dentist preferences and need not be developed in detail here as the point is that a surgical trajectory may be created based upon the modifications to the restorative trajectory deemed prudent by the dentist. A significant amount of information is acquired by having a two-dimensional X-ray taken with respect to a known coordinate system established by the guide sleeve 180 as positioned by the cartridge 150 created based on the restorative trajectory 804.

The drilling depth to be used for the osteotomy is selected based on the proposed distance between the coronal face 196 of the guide sleeve 180 and the intended apical depth of the implant 750. This distance is the sum of the distances between the coronal face 196 of the guide sleeve 180 and the bone crest 854 and the length of the selected implant 750 (assuming a zero millimeter offset between the coronal face 754 of the implant 750 and the bone crest 854).

Bone Volume Contour.

Figure 15:
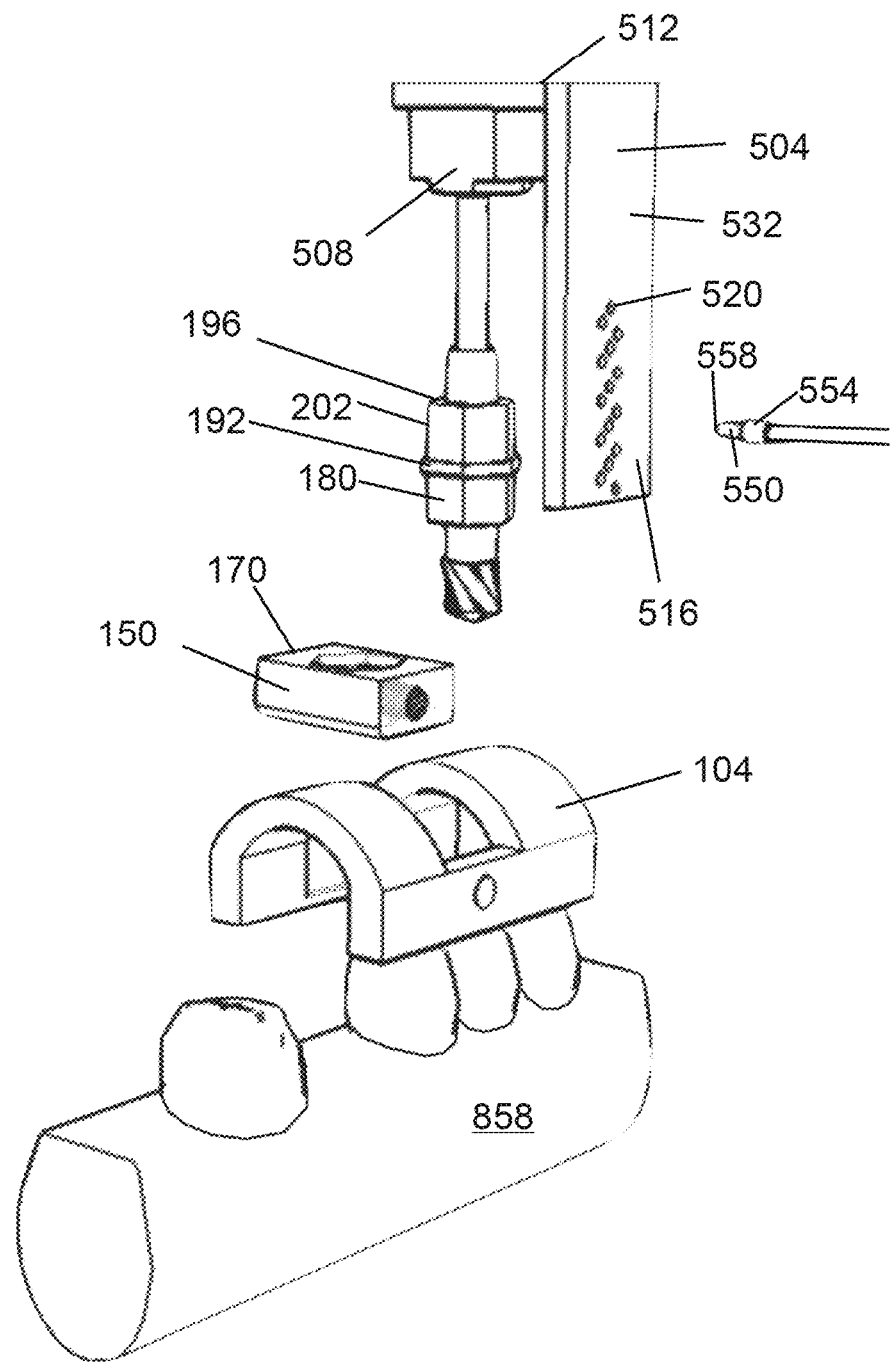
FIG. 15 is a perspective view of an exploded diagram that introduces the measurement jig for collecting bone volume contour information.

Moving to FIG. 15, it is useful to get a profile of the bone volume in the inner-outer 704 by apical-coronal 712 plane that contains the restorative trajectory 804. This may be accomplished with precision by placing a measurement jig 504 in a known location relative to the known location of the coronal section 202 of the guide sleeve 180. The stop flange 192 of the guide sleeve 180 fits within a stop flange perimeter 166 (See FIG. 12) to rest on a stop flange plane 162 (See FIG. 12) within cartridge 150 so that the coronal side of the stop flange 192 is flush with a coronal face 170 of the cartridge 150. A female hex 508 of the measurement jig 504 fits over the coronal section 202 of the guide sleeve and flush with the coronal face 170 of the cartridge. A spacer arm 512 sets the array arm 516 a known offset from the restorative trajectory 804. A probe tip 558 of measuring pin 550 may be inserted through a pin guide 520 in the array arm 516 to move a collar 554 relative to the probe tip 558. When the probe tip 558 is pressed through the soft tissue 858 to the edge of the bone volume 850 (not shown here), the precise location of the edge of the bone volume 850 at a known apical offset from the coronal face 196 of the guide sleeve 180 may be discerned from the movement of the collar 554. Repeating this process for a variety of apical offsets and on both the outer and inner side of the bone volume 850 provides a two-dimensional contour of the bone volume 850 in the inner-outer 704 by apical-coronal 712 plane that includes the restorative trajectory 804.

One of skill in the art will recognized that bone volume contour readings for planes parallel to the plane containing the restorative trajectory 804 could be used to provide an approximation of the bone volume contour in the plane containing the restorative trajectory. Thus a series of readings a small delta mesial of the plane containing the restorative trajectory might be used. Alternatively, a series of readings a small delta distal of the plane containing the restorative trajectory may be used. An average of readings taken slightly mesial and distal to the plane containing the restorative trajectory may be used.

Figure 16:
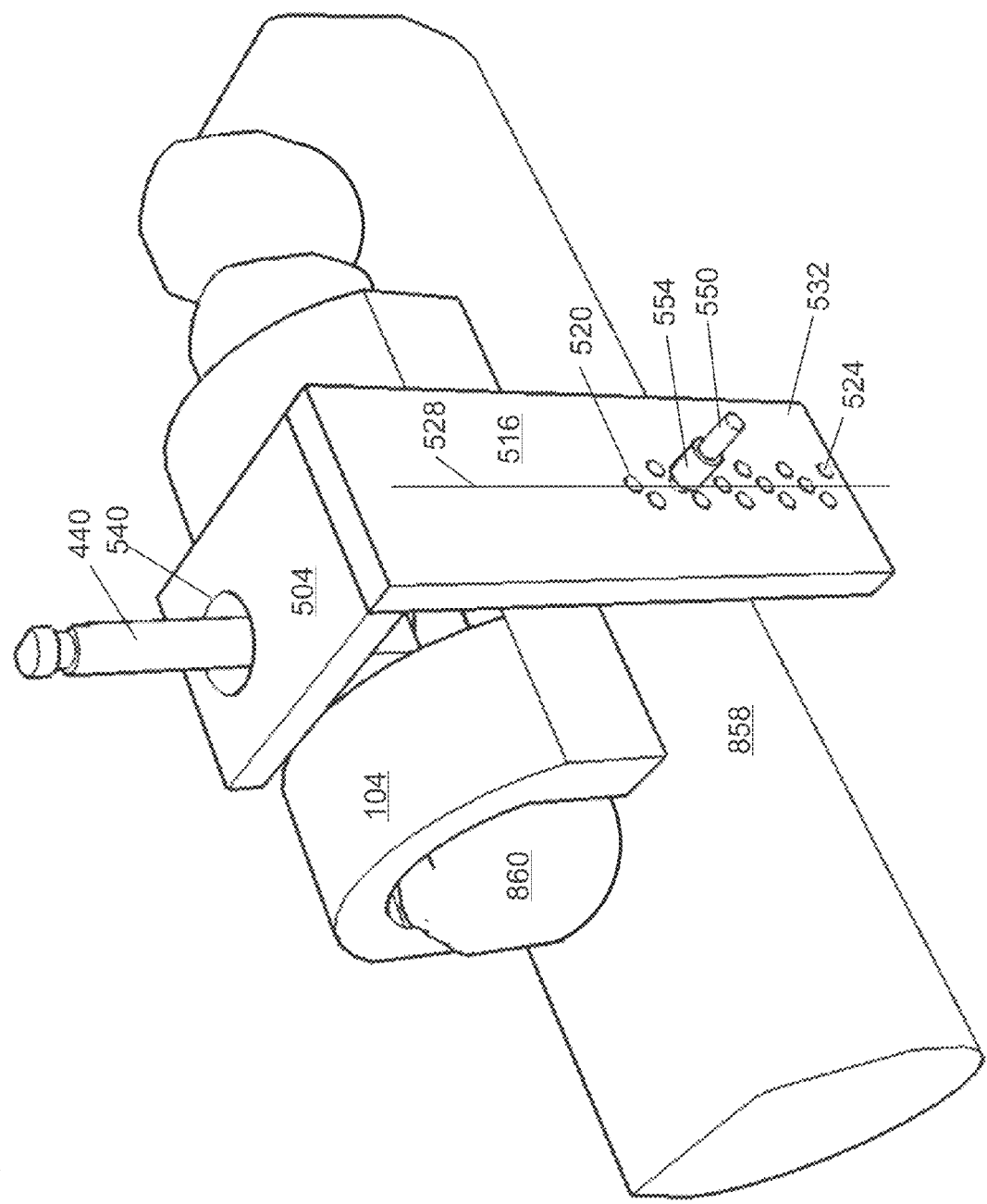
FIG. 16 provides an outer-coronal perspective view of a measuring jig placed for taking of measurements.

FIG. 16 provides a perspective view of a measuring jig 504 placed for taking of measurements. The array arm 516 of the measurement jig 504 has a series of pin guides 520 arranged on midline 528 allow bone contour measurements to be taken in the plane containing the restorative trajectory 804. The measuring pin 550 is shown with probe tip 558 not visible as the probe tip 558 is inserted through the collar-side face 532 of the array arm 516. Additional pin guides 524 may be added distally and mesially of the midline 528 in the event that a dentist wishes to get additional readings. This may be useful if the planning process has moved the intermediate trajectory 812 distally or mesially relative to the restorative trajectory 804 in response to the input from the X-ray.

A bore 540 aligned with the restorative trajectory 804 allows a guide sleeve caddy such as drill bit 440 to be used to place the guide sleeve 180 in the cartridge 150 and then remain in place as the measuring jig 504 is put into place and used.

Figure 17:
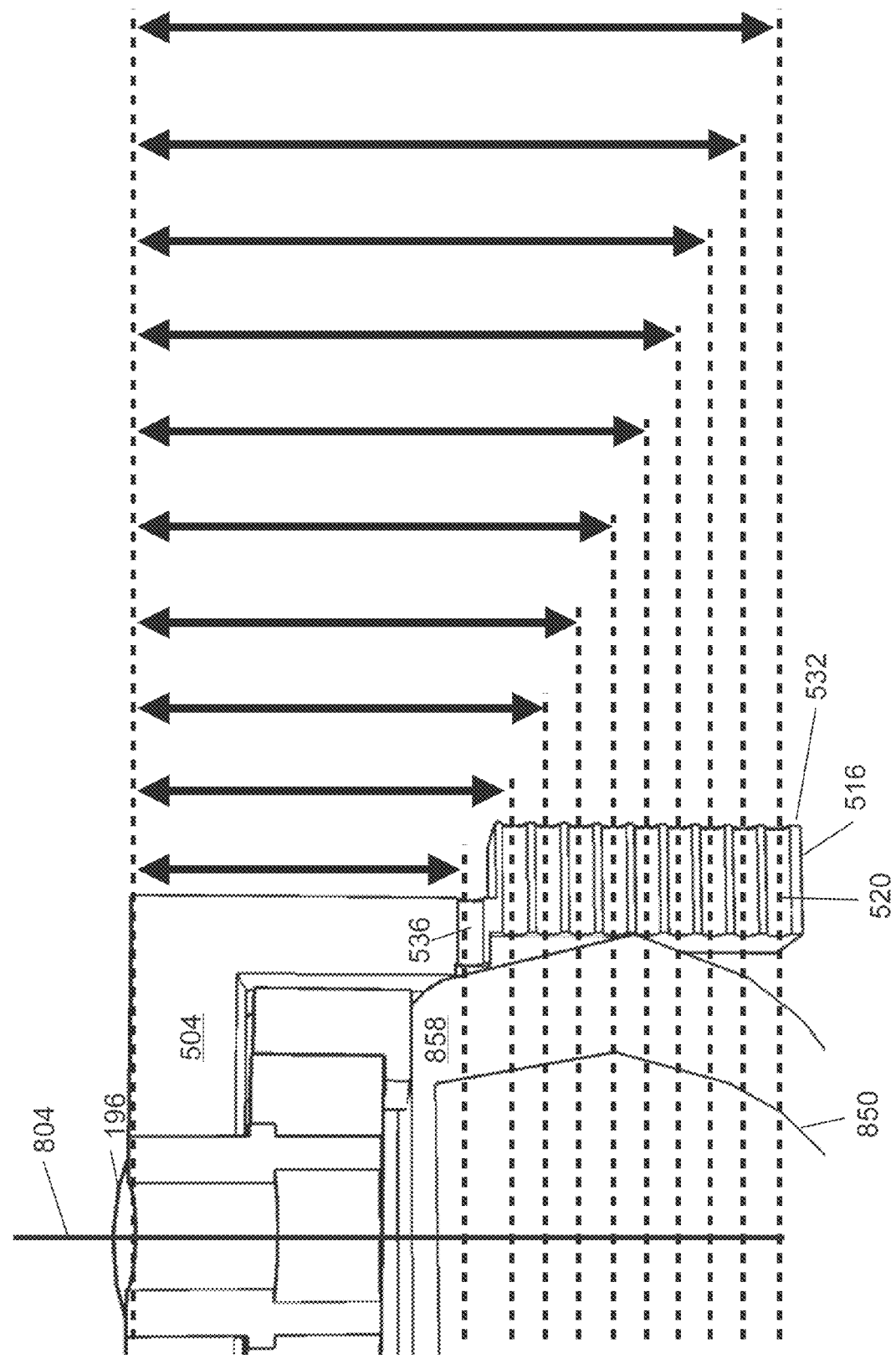
FIG. 17 shows an example of an array of bone volume contour points obtained from use of an alternative measuring jig.

FIG. 17 shows an example of an array of bone volume contour points obtained from use of an alternative measuring jig 504. The measuring jig 504 shown in FIG. 17 differs from the measuring jig 504 shown in FIG. 15 and FIG. 16 in that the array arm 516 is not flat with a single plane for the collar-side face 532 but is stepped to partially approximate the surface of the soft tissue 858. The operation of the alternative measuring jig 504 is the same as discussed above. A probe tip 558 (not shown here) of a measuring pin 550 (not shown here) is moved towards the restorative trajectory 804 through a pin guide 520 which separates the collar 554 (not shown here) from the probe tip 558 (not shown here) and provides a distance separating the edge of the bone volume 850 from the collar-side face 532. The difference being that the collar-side face 532 for pin guide 536 is closer to the restorative trajectory 804 than is the collar-side face for other pin guides 520. However, as the differences are known to the planning software, the differences are handled.

The coronal end of the female hex 508 and spacer arm 512 is not shown in FIG. 17 so that the coronal face 196 of the guide sleeve 180 may be indicated. The software may use the intersection of the restorative trajectory 804 with the coronal face 196 of the guide sleeve 180 as the 0,0,0 point for the coordinate system for inner-outer axis 704, distal-mesial axis 708, and apical-coronal axis 712. As the midline 528 (see FIG. 16) of the array arm 516 is parallel with the restorative trajectory 804, and the apical offsets of the various pin guides 520 relative to the coronal face 196 of the guide sleeve 180 are known, the array of measurements of the distances from the collar-side face 532 yield a contour of the bone volume 850 in the inner-outer 704 by apical-coronal 712 plane.

Figure 18:
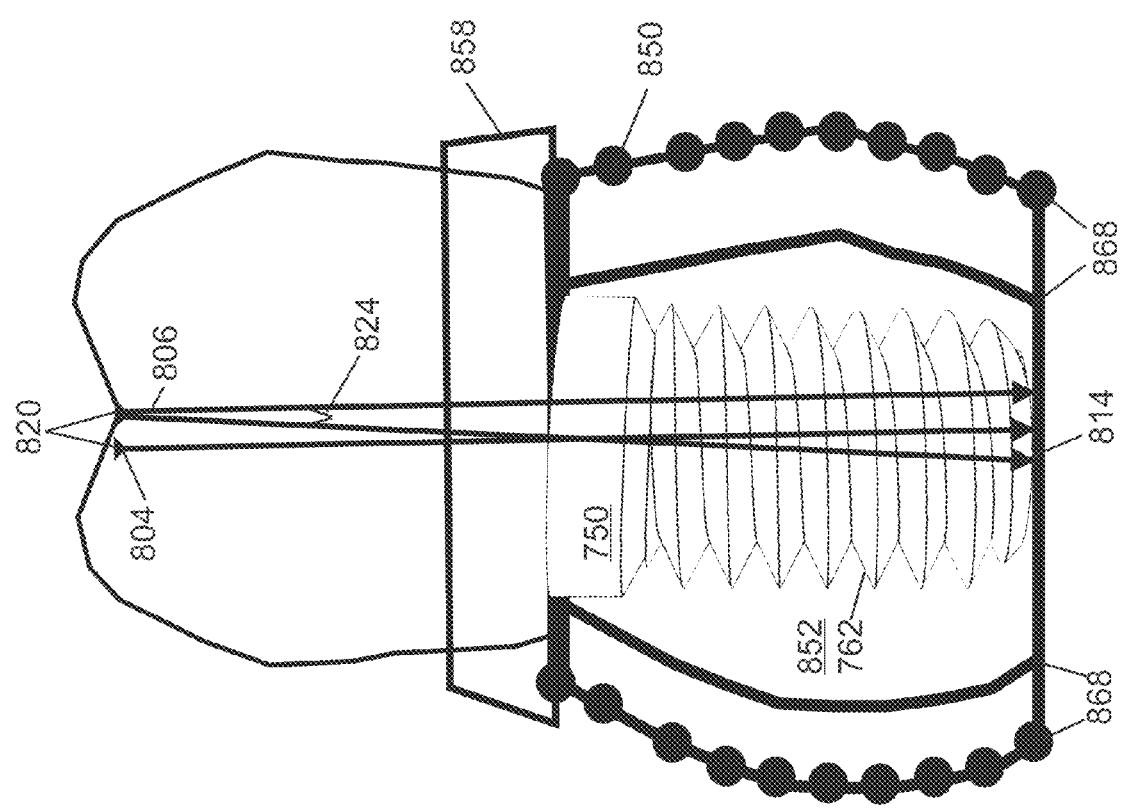
FIG. 18 shows a planning model that has the arrays of measurements providing a contour of bone volume

FIG. 18 shows a planning model that has the arrays of measurements providing a contour of bone volume 850 in the inner-outer 704 by apical-coronal 712 plane containing the restorative trajectory 804. Offsets 868 are used to create a safe bone volume 852. The offset 868 on the outer side does not have to be equal to the offset 868 on the inner side.

If the current trajectory and selected dimensions for the proposed implant 750 do not fit within the safe bone volume 852, then one or more adjustments may be made including:

Reducing a generous offset 868 a bit to expand the safe bone volume 852;

Reducing the major diameter of the threads 762 on the proposed Implant 750;

Moving the trajectory on the inner-outer axis 704 to better center the implant 750 in the safe bone volume 852; and Tilting the trajectory away from the apical-coronal axis to move the apical end 758 of the implant away from the closer edge of safe bone volume 852.

Thus, FIG. 18 shows an intermediate trajectory 812 which has been moved by offset 820. Offset trajectory 806 is then tilted by angle 824 versus the offset trajectory 806. Note that the offset and angulation in the inner-outer 704 by apical-coronal 712 plane would not be visible in a view of the distal-mesial 708 by apical-coronal 712 plane. Likewise, an earlier translation or angulation of the trajectory made in response to the two-dimensional X-ray would not be visible in FIG. 18. Thus the restorative trajectory may be modified by a distal-mesial offset, a distal-mesial angulation, an inner-outer offset, and an inner-outer angulation. While the depth and width of the drilled bore is not part of the surgical trajectory 814, these features are part of the surgical plan. The depth and width of the bore for the implant may also be modified during the planning process for the surgical trajectory.

Using the coronal face 196 of the guide sleeve 180 as a drill stop allows the depth of the drilling process to be controlled by the combination of the apical-coronal height of the surgical cartridge 150, the positioning of the chamber 108 in the frame 104, and the apical-coronal height of the guide sleeve 180. The desired depth is a function of the total bone volume 850 and offset resulting in safe bone volume 852 and a nominal length of implant 750 from the coronal face of the implant 750 which is often set at the bone crest 854.

The order of modifying the restorative trajectory 804 to various intermediate trajectories and a final surgical trajectory 814 can be done with the distal-mesial corrections first or with the inner-outer corrections first. The corrections in one plane are made independent of the corrections in the other plane.

Thus, at this stage in the process, the restorative trajectory 804 is modified by the anatomic inputs from a two-dimensional X-ray that is taken in a known orientation with respect with the restorative trajectory 804. A bone contour is obtained transverse to the two-dimensional X-ray. The combination of the inputs combined with the planning stage three-dimensional X-ray obviates a need for a three-dimensional X-ray after the frame 104, cartridge 150, and guide sleeve 180 are in place.

One of skill in the art will recognize that it is at least possible that no substantive changes need be made to the restorative trajectory 804 and the restorative trajectory 804 is confirmed as appropriate for use as the surgical trajectory 814. At that time the cartridge 150 would effectively become the surgical cartridge 149.

Surgical Cartridge.

A digital file is sent to a device to create the surgical cartridge 149 with the surgical trajectory 814. Note that the surgical cartridge 149 may differ from the cartridge 150 for the restorative trajectory 804 in that the centerline of the surgical trajectory 814 may be offset from the centerline of the coronal face 170 of the surgical cartridge 149. Further, the surgical trajectory 814 may not be perpendicular relative to the apical face 174 of the surgical cartridge 149. The coronal face 170 of the surgical cartridge 149 may not be parallel to the apical face 174 of the surgical cartridge 149 in order to provide any desired angulation in either or both of the distal-mesial 708 direction or the inner-outer 704 direction. However, surgical trajectory 814 that is not perpendicular to the apical face 174 of the surgical cartridge 149 could be implemented in a surgical cartridge 149 with a coronal face 170 parallel to the apical face 174 as the opening 154 does not have to be perpendicular with the coronal face 170 and the stop flange perimeter 166 could be interrupted by the coronal face 170. The female hex sleeve 432 for the spacer arm 416 used for alignment of the X-ray guide ring 408 may be given a thickness that rests on the coronal face of the stop flange 192 and thus would not need to abut the coronal face 170 of the surgical cartridge 149. Likewise the female hex 508 on the measuring jig 504 can have a width of more than the coronal face of the stop flange 192. For example the coronal face of the stop flange 192 may protrude out 0.5 millimeters around the perimeter of the guide sleeve 180.

Drill Irrigation Ports.

Figure 19:
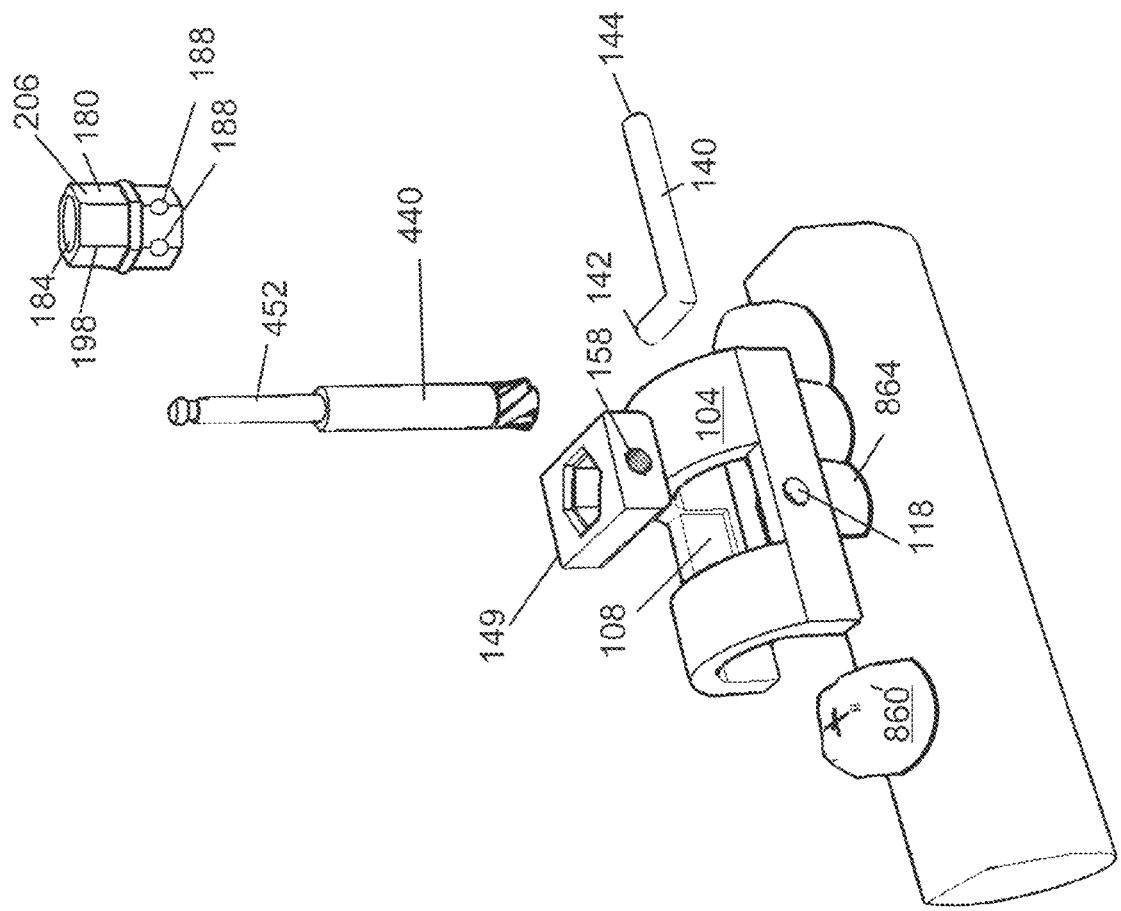
FIG. 19 is an outer-coronal perspective view of an exploded diagram that includes the surgical cartridge and shows the optional irrigation ports.

The surgical cartridge 149 may be created with at least one irrigation bore 158. Thus it is useful to describe the optional drill irrigation feature at this time. This feature is visible in FIG. 19 and FIG. 12 (which uses a cartridge 150). In order to provide cooling irrigation to the drilling process to remove heat from the bone volume 850 during the drilling process, irrigation fluids may be provided. More specifically, the irrigation fluids may be provided to the bore 184 in the guide sleeve 180 through an irrigation bore 188 aligned with the outer hex ridge 198 and in the apical section 206 of the guide sleeve 180. Optionally, there may be a set of two to six irrigation bores 188 so that multiple orientations of the guide sleeve 180 within the surgical cartridge 149 align an irrigation bore 188 with the irrigation system. An irrigation bore 188 needs to be aligned with an irrigation bore 158 in the surgical cartridge 149 and an irrigation bore 118 in the frame 104. An irrigation tube 140 is used to provide irrigation during the surgical procedure to the irrigation bore 118 in the frame 104.

As the irrigation bore 158 in the surgical cartridge 149 needs to be aligned with the irrigation bore 118 in the frame 104, the irrigation bore 158 provides an indication of proper orientation of the surgical cartridge 149 in the chamber 108 of the frame 104. Alternatively, the chamber 108 in the frame 104 and the shape of cartridges 150 and 149 can be created so that only one possible insertion orientation is possible.

One of skill in the art will recognize that the irrigation tube 140 will provide a connection end 144 away from the surgical site so that a flexible tube (not shown here) can be connected to the connection end 144 to provide irrigation fluids. The irrigation tube 140 may be made of stainless steel so that it may be sterilized and reused. The insertion end 142 of the irrigation tube 140 may mate with the irrigation bore 118 of the frame 104 and with the irrigation bore 158 in the surgical cartridge 149. The insertion end 142 of the irrigation tube 140 may be used to lock the cartridge 150 or 149 with the frame 104. Ideally, the insertion end 142 of the irrigation tube 140 does not enter into the irrigation bore 188 of the guide sleeve 180 so that the guide sleeve 180 may be inserted or removed without removing the irrigation tube 140. Thus, the diameter of irrigation bore 188 is markedly different from the diameters of irrigation bore 158.

Modified Height for Use as Drill Stop.

Note—optionally, the surgical cartridge 149 with the surgical trajectory 814 may be designed to raise the coronal face 170 of the surgical cartridge 149 so that the coronal face 196 of the guide sleeve 180 is elevated so that the coronal face 196 of the guide sleeve 180 serves as a drill stop to limit the apical travel of the drill bit 440 to prevent creating a deeper bore in the bone than intended. The drill would need to have a leading face that makes contact with the coronal face 196 of the guide sleeve 180 to limit the apical movement of the distal cutting section 444 of the drill bit 440.

Alternatively a combination of a different nominal height guide sleeve 180 and an adjusted surgical cartridge 149 can be used to place the coronal face 196 of the guide sleeve 180 at an appropriate height to be a drill stop.

Confirming Bone Contour.

Some dentists may wish to take bone contour measurements with the surgical cartridge 150 used to position the guide sleeve 180 to bolster confidence that the surgical cartridge 150 was manufactured as intended and that the process has led to a surgical trajectory 814 that should be used for a drilling process.

Confirming X-Ray.

Once the surgical cartridge 149 is created and inserted into the frame 104 which was left as originally positioned, some dentists may choose to take an additional X-ray to confirm the positioning. This process would be much like the process described above except that the female hex sleeve 432 will engaged with a guide sleeve oriented for the surgical trajectory 814 rather than the original restorative trajectory 804. Other measurement tools may be aligned with the guide sleeve 180 in the manner described above.

Likewise, the dentist may wish to take an X-ray after doing some drilling with a narrower drill bit before drilling with a longer and wider drill bit.

Drilling.

Figure 20:
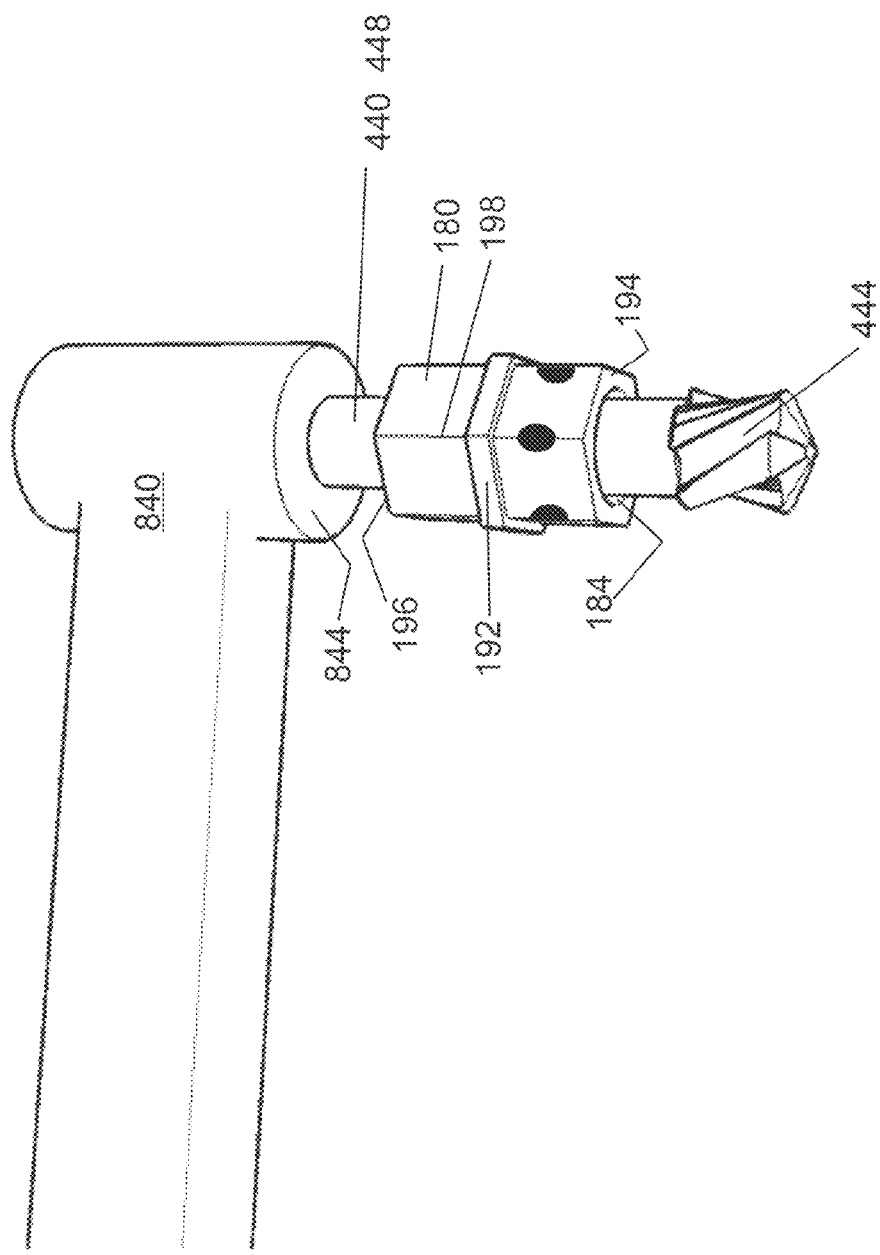
FIG. 20 shows a drill drive 840 engaged with a drill bit 440 that is engaged with a guide sleeve 180.

FIG. 20 shows a drill drive 840 engaged with a drill bit 440 that is engaged with a guide sleeve 180. Visible portions of the drill bit 440 include the intermediate section 448, and distal cutting section 444. As discussed above, the maximum width of the distal cutting section 444 is too large to travel through the entire bore 184 of the guide sleeve 180 so that the guide sleeve 180 is captured and retained by the drill bit 440. Optionally, the irrigation fluids may be delivered only while the drill bit is rotating by linking the drill to the system that provided irrigation fluids. The height of the coronal face 196 of the guide sleeve 180 may be set to be a drill stop to stop the stop surface 844 of the drill drive 840.

Other elements of guide sleeve 180 visible in FIG. 20 include coronal face 196, stop flange 192, outer hex ridge 198, and apical face 194.

A sequence of guide sleeves 180 with progressively larger bores 184 may be provided to work with a set of drill bits 440 with distal cutting sections 444 and intermediate sections 448 that have progressively larger diameters. Typically, the widest drill bit 440 will drill a bore not wider than the minor diameter of the threaded portion of the implant 750 so that the threads 762 on the implant 750 may engage with bone volume 850. The bores 184 of the sequence of guide sleeves 180 may be designed to provide adequate maintenance of the intended surgical trajectory 814 by the interaction of the bore 184 towards the coronal face 196 of the guide sleeve 180 while retaining the ability to withdraw the distal cutting section 444 into an expanded bore 210 towards the apical face 194 of the guide sleeve 180. Having the ability to at least partially withdraw the distal cutting section 444 into the expanded bore 210 allows the guide sleeve 180 to be fully seated in the surgical cartridge 149 before the distal cutting section 444 is advanced into the bone volume 850.

One of skill in the art will appreciate that for an implant 750 large major diameter on the threads 762, a greater number of progressively larger drill bits 440 and guide sleeves 180 with progressively larger bores 184 will be used. However, the size of the stop flange 192 remains constant as the surgical cartridge 149 remains constant throughout the drilling process. Thus, the opening 154 in the surgical cartridge 149 is set based upon the selected major diameter for the implant 750 so that appropriate size drill bits 440 may be accommodated in an appropriate family of guide sleeves 180 that differ only in the size of the bores 184.

The drilling process may initially use a first drill length and then switch to one or more longer drill lengths. For example the initial drill length may be extended 5 millimeters to a subsequent drill length.

If a post drilling X-ray is desired, then an egress arm 420 with an appropriately sized female hex sleeve 432 must be used with the particular size of the guide sleeve family in use.

Process Steps.

Figure 21:
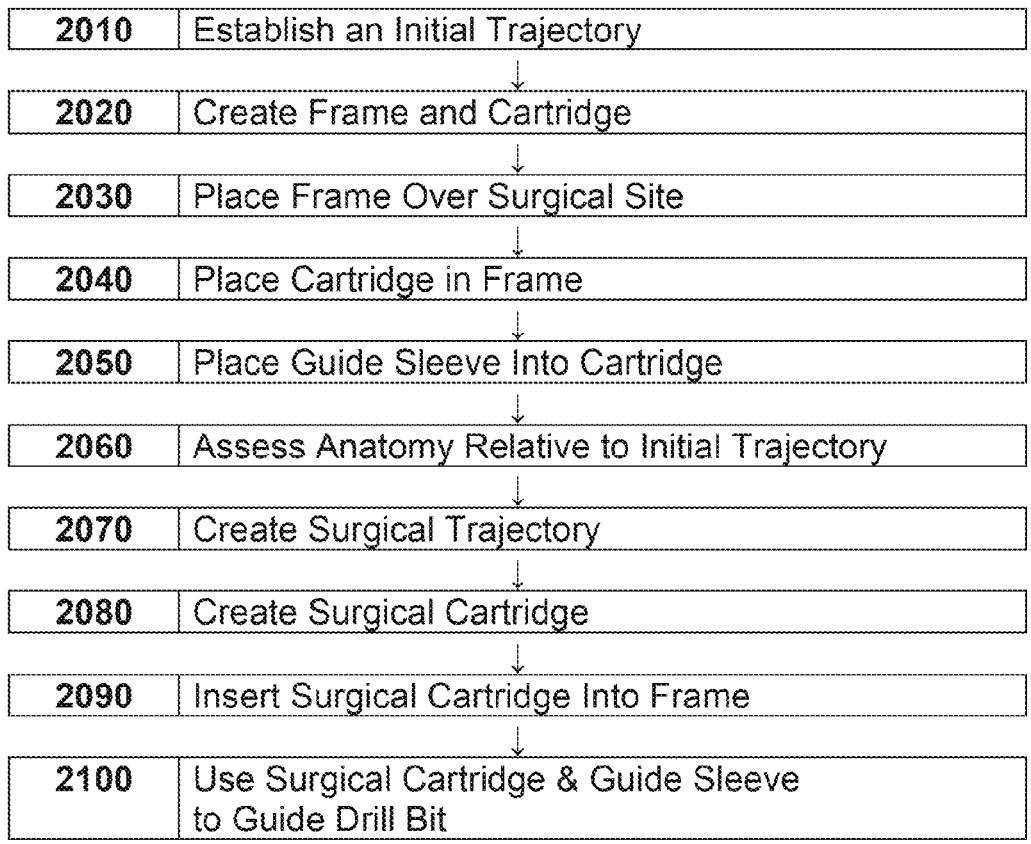
FIG. 21 sets forth the flowchart for the high level process steps for a sequence to guide one or more drill bits along a surgical trajectory for an implant.
Figure 22:
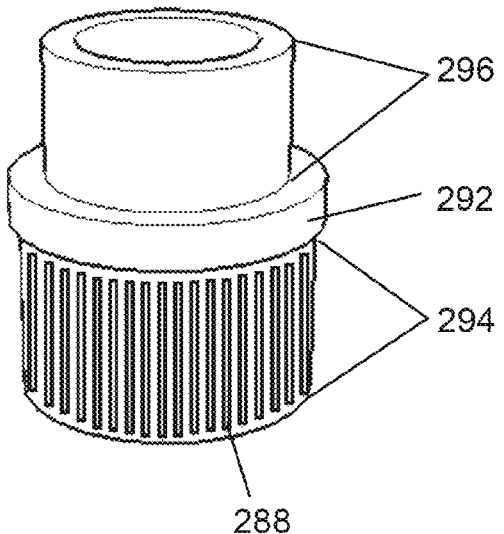
FIG. 22 shows an alternative round guide sleeve with irrigation slots.

FIG. 21 sets forth the flowchart 2000 for the high level process steps for a sequence to guide one or more drill bits 440 along a surgical trajectory 814 for an implant 750.

Step 2010—Establish an Initial Trajectory. Using protocols known to those of skill in the art, determine a trajectory for a bore to provide an implant placement. This initial trajectory may be determined by the anatomical needs for restoring form and function with no regard to the available anatomical structures for osseointegration of the implant. Or it may be an initial estimate of a surgical trajectory which is tuned by the measurements taken from a guide sleeve oriented along this initial trajectory.

Step 2020—Create Frame & Cartridge. Create frame 104 and cartridge 150 based upon the initial which may be the restorative trajectory. The cartridge 150 is designed to receive a guide sleeve 180.

Step 2030—Place frame over surgical site.

Step 2040—Place Cartridge in Frame. One of skill in the art will recognize that the cartridge 150 may be placed into the frame 104 before the frame 104 is placed within the mouth of the patient.

Step 2050—Place Guide Sleeve Into Cartridge. One of skill in the art will recognize that the guide sleeve 180 may be placed into the cartridge 150 before the cartridge is placed within the mouth of the patient. However, it is likely that the guide sleeve 180 will be conveyed to the cartridge 150 after the frame 104 and cartridge 150 are in place.

Step 2060—Assess Anatomy Relative to Initial Trajectory. The present disclosure teaches specific tools to assess the position of bone volume and look for other anatomic features relative to the initial trajectory. Those of skill in the art may use the disclosed tools or other tools to assess the bone volume and other relevant anatomy using any tools known to those of skill in the art.

Step 2070—Create Surgical Trajectory. Using measurements to discern positions of relevant anatomy relative to the initial trajectory and intermediate trajectories 806 to create a surgical trajectory 814.

Step 2080—Create a Surgical Cartridge. Using the surgical trajectory 814 and a desired limit on the depth of a bore created to receive the implant, create a surgical cartridge 149 for use in orienting drill bits 440 to create a desired bore.

Step 2090—Insert Surgical Cartridge into Frame.

Step 2100—Use Surgical Cartridge with at least one Guide Sleeve to Guide Drill Bit. Frequently, there will be a sequence of guide sleeves 180 that are used. The guide sleeves 180 are placed so the longitudinal centerline of the guide sleeve 180 defines the surgical trajectory 814 for the drilling process. A series of drills bits 440 may be used to drill a sequence of bores along the surgical trajectory 814. As is known in the art, the drill bits 440 may increase in diameter to drill an appropriate sized bored for the planned implant 750. A series of guide sleeves 180 with bores 184 of increasing diameter maintain the alignment of the series of drill bits 440 along the surgical trajectory 814.

The surgical cartridge 149 may be sized to work with the guide sleeves 180 to serve as a drill stop so that the drill bit 440 may only move apically a prescribed distance before the drill body contacts the coronal face 196 of the guide sleeve 180 to limit further apical travel of the distal cutting section 444 of the drill bit 440.

Preferred Additive Manufacturing Process & Materials.

Those of skill in the art will recognize that many additive manufacturing processes may be used to create a cartridge 150 or surgical cartridge 149. One suitable choice is a fused filament fabrication printer using polylactic acid (commonly known as PLA). FDA compliant PLA is used in many other medical applications and if left in the body will safely degrade over time to lactic acid. The material used for cartridges (150, 149) may be used for frames 104. The frame 104 and initial cartridge 150 may be printed in approximately thirty minutes. A subsequent cartridge may be printed in approximately ten minutes.

Alternatives and Variations.

Frames.

The frames 104 shown in the various drawings for this disclosure straddle at least one tooth on either side of the intended site for the implant 750. In some instances, the implant will be intended to place a prosthetic tooth on what would be the most distal tooth for the quadrant. In such a case, the frame won't extend distally to engage a more distal tooth. The frame 104 may be extended on the mesial side to engage with several mesial side teeth to provide a stable base for the surgical cartridge 149 and work on the surgical site. A portion of the frame 104 may extend distally and rest on the soft tissue surface 862. The frame 104 may be pinned or otherwise affixed to the soft tissue surface 862.

In cases where the implant 750 is not destined for the last tooth in a quadrant but one of the adjacent teeth to the intended surgical site is missing, the frame 104 may be adjusted to fit the soft tissue 858 that is present.

Alternative Anchor Points for Measurement Assemblies.

As discussed within this disclosure, assemblies for measurements may be anchored and placed in a known orientation with respect to a trajectory by using a female sleeve to engage a coronal portion of a guide sleeve 180 placed within a cartridge 150 or 149. This focus on one solution does not mean that other anchor/orientation options are not available. The anchor/orientation may be achieved through an interaction of the measurement assembly and a portion of the guide sleeve other than the coronal portion of the guide sleeve. The anchor/orientation may be achieved through an interaction independent of the guide sleeve but dependent on one or more engagement features on the cartridge 150 or 149 or the frame 104. The one or more engagement features may be protrusions extending from the cartridge 150 or 149 or the frame 104. The one or more engagement features may be bores or other openings in the cartridge 150 or 149 or the frame 104.

The anchor/orientation may be achieved by some combination of engagement features on the cartridge 150 or 149 and the frame 104.

Using an Instrument Guide.

One of skill in the art will appreciate that unless the instrument assembly uses the coronal to apical bore 184 of the guide sleeve 180, that an instrument guide without the capacity to be used as a drill bit guide sleeve may be inserted into the opening that receives the guide sleeve 180 whether that opening is in a cartridge 150 or 149, or in a contact surface as discussed above. As long as the instrument guide allows an instrument assembly to engage the instrument guide so as to position the instrument assembly in a known relationship with a specific trajectory into the jawbone of the patient, the teachings of this disclosure with respect to the alignment system 400 taking X-rays or measurement jig for taking bone contour readings may be used.

Use of Guide Sleeve to Position Measurement Devices.

As discussed above, the prior art includes a system art which had two main components, the guide sleeves and the contact surface. The contact surface provides a custom fit with the patient's mouth (gums, jawbone, and teeth). One or more guide sleeves (sometimes guide cylinders) within the drill guide are used to orient and guide the drilling system to create a bore at the desired location and with the desired angulation (distal-mesial and inner-outer). This system lacked the many advantages set forth above. However, one of skill in the art could implement some of the teachings set forth above by modifying the guide sleeve and the bore in the contact surface to use a guide sleeve with a non-circular outer perimeter. For example if the guide sleeve 180 of the present disclosure was used in a contact surface with a corresponding opening 154, stop flange plane 162 and stop flange perimeter 166, then the contact surface with imbedded guide sleeve 180 could be used to support the structures described above for collecting X-ray and bone contour information, or any other measurement assembly. The measurements would have a known relationship to the centerline of the bore in the guide sleeve 180 as described above.

Direct Placement of Instrument Assembly into Contact Surface.

One of skill in the art will appreciate that instead of having the instrument assembly interact with guide sleeve 180 or an instrument guide that the instrument assembly could interact directly with the contact surface or cartridge 150 or 149. One option would be to have an end of the instrument assembly fit into the contact surface or cartridge (150 or 149) in the same manner as does a guide sleeve 180. Thus, the end of the instrument assembly may emulate at least a portion of the apical end of a guide sleeve 180 so that the instrument assembly is precluded from rotation relative to the contact surface or cartridge 150 or 149.

Measuring Device Assemblies not Mounted onto the Initial Assembly.

This disclosure sets forth the advantages of mounting measurement device assemblies in a fixed relationship with at least some portion of the guide sleeve, instrument guide, opening for receipt of the guide sleeve, or features on the cartridge or frame. Those of skill in the art wishing to take advantage of some other teachings of the present disclosure could obtain measurements, particularly images of a guide sleeve in an initial cartridge. Those of skill in the art will recognize that the use of a guide sleeve that is at least part radiopaque may be used to provide an indication of relationship between the obtained measurements and the initial linear trajectory. This same process could be used to obtain images keyed to the surgical linear trajectory after the surgical cartridge is in place.

Order of Obtaining Measurements.

The present disclosure does not preclude obtaining X-Ray information relative to the frame 104 and cartridge 150 or 149 after obtaining bone volume contour information.

Drill Bits.

An alternative to the drill bit 440 shown throughout this disclosure would be to use a spherical burr bit. While the spherical burr may not be entirely withdrawn into the guide sleeve 180, use of the spherical burr bit before the guide sleeve is fully seated is not a problem as a spherical burr bit does not create a trajectory that binds the path of the bit in the way that a twist drill bit does. One of skill in the art could select other drill bits suitable for use in bone. While one may use a drill bit that is wider at the distal end to caddy the guide sleeve, this is not required as one can handle the guide sleeve 180 to insert and remove the guide sleeve 180 from the cartridge 150 or 149.

Irrigation.

Irrigation fluid may be provided to the surgical site to dissipate heat from the drilling process. The irrigation may be provided as taught in this disclosure. Alternative forms of irrigation, including irrigation through an interior channel within the drill bit may be used.

Alternative Manufacturing of Cartridges.

The disclosure teaches the use of additive manufacturing processes to create the cartridge 150 and surgical cartridge 149 by a computer aided machining process that removes material from a blank rather than adds material. For example, blanks with hexagonal bores could be machined so that the bore which was initially centered in the face of the blank and perpendicular to the top and bottom of the blank may now be off-center and angulated relative to the apical face of the surgical cartridge 149 manufactured in this manner. The computer aided manufacturing process could cut the recess to receive the stop flange 192 of the guide sleeve 180.

Those of skill in the art will recognize that other manufacturing processes may be used to form cartridges and the teachings of the present disclosure are not limited to the use of additive manufacturing processes or any specific manufacturing process. For example, the cartridges may be formed using a CNC router (computer numerical control router). The teachings of the present disclosure favor a process which can be done quickly in the dental office so that the surgical cartridge 149 may be made soon after taking the measurements using a guide sleeve in the restorative cartridge.

Retention of Cartridge in Frame.

The retention of the cartridge 149 or 150 in the chamber 108 of frame 104 may be achieved by having the cartridge 149 or 150 fit precisely into the chamber 108. The retention may be augmented as noted elsewhere by mating the insertion end 142 of the irrigation tube 140 with the irrigation bore 158 of the cartridge 149 or 150 to maintain the alignment of the irrigation bore 158 of the cartridge 149 or 150 with the irrigation bore 118 of the frame 104.

Additional tools are available for enhancing the retention of the cartridge 149 or 150 with the frame 104 such as adding grooved surfaces to the chamber 108 and the cartridge 149 or 150 so that the chamber 108 of the frame 104 needs to flex in order to allow movement of the cartridge 149 or 150 into or out of the chamber 108. There are many options available for a snap lock effect to hold one piece relative to another that are known to those of skill in the art.

Multiple Guide Sleeves in a Cartridge.

Although, the figures discussed in this disclosure have shown a single opening 154 in the cartridge 150 or surgical cartridge 149, one could have an elongated cartridge with more than one opening 154 to receive more than one guide sleeve 180.

Mandible or Maxilla.

While the drawings used to disclose selected teachings of the present disclosure were consistently oriented to suggest that the surgical site was on the lower jaw (mandible), the teachings of the present disclosure are not limited to use on the lower jaw or to any specific tooth position. The teachings may be used for implants placed in the upper jaw (maxilla).

Alternative Orientations of Cartridge.

The present disclosure suggests aligning an opening in the cartridge 150 so as to put the centerline of the bore 184 in the guide sleeve 180 co-linear with the restorative trajectory 804. One of skill in the art will recognize that as the benefit of this process is to precisely position measurement devices such as two-dimensional X-ray assemblies or bone volume contour measurement jigs 504, then the cartridge 150 could position a centerline of the guide sleeve 180 a fixed amount of translation or angulation in one or more planes as long as the assemblies made an equal and opposite adjustment to bring the measurement process back to the plane of interest.

X-Ray Sensor.

The disclosure implies that the X-ray sensor is adapted to provide a digital file. One of skill in the art can appreciate that an X-ray sensor could be an X-ray film that responds to the exposure to X-rays and then is subsequently used in a chain of processes that lead to a digital file used in the planning software.

Imperfect Alignment of X-Ray.

One of skill in the art will appreciate that an alignment system 400 could be implemented that fails to position a centerline of a guide ring 408 co-linear with the inner-outer axis 704. Thus, the guide ring 408 may be offset a known distance mesially, distally, apically, or coronally. The guide ring 408 may also be angled relative to the true inner-outer axis 704. These misalignments introduce imperfections into the two-dimensional X-ray but perfection is not required. The offsets between total bone volume 850 and safe bone volume 852 more than compensate for small imperfections.

Use of Three-Dimensional X-Ray.

While the present disclosure provides a method for obtaining adequate information without seeking a three-dimensional X-ray after placing the guide sleeve 180 into the cartridge 150 in frame 104, the use of a three-dimensional X-ray is not excluded by the teachings of this disclosure. One could obtain a three-dimensional X-ray after the frame 104, cartridge 150 or 149, and guide sleeve 180 were in place. The three-dimensional X-ray could be combined with the digital model of the surgical site as the guide sleeve 180 is apt to be obtuse to X-rays and serve as a landmark to allow for alignment of the three-dimensional X-ray with the existing three-dimensional model to allow the model to be augmented.

Positioning of the Centerline of the Guide Sleeve Bore.

While the disclosure has provided examples where the centerline of the bore 184 in the guide sleeve 180 is co-linear with a coronal to apical centerline of the guide sleeve 180, a co-linear relationship is not required. For example, the centerline of the bore 184 may be set parallel to the coronal to apical centerline of the guide sleeve as long as the offset between the two centerlines are known. The offset may include an inner-outer offset and a distal-mesial offset. Thus, the term aligned is not limited to co-linear.

Precluding Rotation.

While the present disclosure has uses a hexagonally shaped coronal section 202 of the guide sleeve 180 with an aligned hexagonal shaped stop flange 192 and an aligned hexagonal apical section 206, this symmetry is not required. One of skill in the art will recognize that the coronal section 202 and the stop flange 192 do not have to have the same shape to work as long as the coronal section 202 fits through the stop flange plane 162. Either the coronal section 202 or the stop flange 192 may be round as the non-round shape of the other section could be used to preclude rotation and allow the guide sleeve 180 to be used to position an instrument assembly including the alignment system 400 or measurement jig 504. Those of skill in the art are familiar with tools to allow a round cylinder to be precluded from rotation including the use of pins, ball & detent mechanisms, and other mechanisms that would allow the guide sleeve 180 to be positioned reliably.

Likewise, a cylindrically shaped apical section 206 of a guide sleeve 180 could be used to anchor to position an instrument assembly including the alignment system 400 or measurement jig 504 through use of a pin, ball & detent mechanisms and other mechanisms that would allow the instrument assembly to be positioned reliably.

One of skill in the art may similarly use a modified instrument guide in the same manner as set forth above to place the instrument assembly in a known relationship with the specific trajectory into the jawbone.

One of skill in the art may take the teachings of the present disclosure and create a modified system that allows an instrument assembly to move from an initial position to another position before locking the instrument assembly so that it may no longer rotate freely around the coronal to apical centerline of the instrument guide or the coronal to apical centerline of the open passageway from a coronal side of the base unit to an apical side of the base unit.

Alternative Guide Sleeve.

While guide sleeve 180 discussed in this disclosure has a apical section 206 and stop flange 192 that are shaped to preclude rotation of the guide sleeve 180 within the cartridge 150 or 149, many of the teachings of the present disclosure may be used with a guide sleeve that is not precluded from rotation within the cartridge.

Guide sleeve 280 has a bore 184 to allow at least a portion of a drill bit to be constrained by the bore 184 in guide sleeve 280 so that a bore is created in a jawbone along the surgical trajectory. The stop flange 292 and apical section 294 are round and thus there is nothing to prevent guide sleeve 280 from rotating within a cartridge built to receive guide sleeve 280. Likewise coronal section 296 is round and is not adapted to preclude an instrument assembly from rotating around the guide sleeve 280 as measurements can be taken without reliance on this feature.

In order to obtain the benefits of irrigation fluid when drilling, a series of irrigation slots 288 are provided within the apical section 294 so that irrigation fluids may be provided through aligned bores in the frame 104 and a cartridge adapted to receive guide sleeve 280.

Other Surgical Sites.

One of ordinary skill in the art will recognize that the teachings of the present disclosure could be used with other surgical sites outside of the patient's mouth which may use a coordinate system suitable for work in that area and thus different from apical-coronal by distal-mesial by inner-outer.

General Comments.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. A method of aligning a drill bit for preparing a bore to receive a dental implant, the method comprising:
    creating a three-dimensional model of a surgical site and selecting an initial linear trajectory for drilling an initial proposed bore;
    creating a frame to position a cartridge coronal to the surgical site, the frame prepared to fit patient anatomy adjacent to the surgical site and having a chamber to receive the cartridge;
    creating an initial cartridge with an opening from a coronal side of the initial cartridge to an apical side of the initial cartridge;
    placing the initial cartridge into the chamber;
    placing a guide sleeve in the opening in the initial cartridge to form an initial assembly, the opening in the initial cartridge sized to constrain an orientation of the guide sleeve so that a longitudinal axis of a coronal to apical bore in the guide sleeve is positioned a known offset from the initial linear trajectory;
    obtaining at least one input with a known relationship to the initial linear trajectory;
    using the at least one input to enhance the three-dimensional model of the surgical site and select a surgical plan to plan a surgical bore with:
    an apical end;
    a coronal end;
    a diameter; and
    a surgical linear trajectory; the surgical bore selected to stay within a bone volume found at the surgical site;
    placing a surgical cartridge into the chamber of the frame; and
    placing a guide sleeve in the surgical cartridge; and
    the guide sleeve is constrained by a coronal to apical opening in the surgical cartridge so that a longitudinal axis of a coronal to apical bore in the guide sleeve is oriented along the surgical linear trajectory such that the guide sleeve may be used to constrain a drilling trajectory of the drill bit along the surgical trajectory.

2. The method of claim 1 wherein obtaining at least one input with the known relationship to the initial linear trajectory includes mounting at least one measuring device assembly onto the initial assembly so that measuring device assembly takes measurements with the known relationship to the initial linear trajectory.

3. The method of claim 1 wherein the at least one input to enhance the three-dimensional model of the surgical site confirms the initial linear trajectory as suitable for the surgical linear trajectory and the initial cartridge is used as the surgical cartridge.

4. The method of claim 1 wherein the at least one input to enhance the three-dimensional model of the surgical site indicates a need to modify the initial linear trajectory so that the surgical linear trajectory differs from the initial linear trajectory and the method includes creating the surgical cartridge and placing the surgical cartridge into the chamber of the frame after removing the initial cartridge.

5. The method of claim 1 wherein the initial linear trajectory is a restorative trajectory unaffected by availability of bone volume.

6. The method of claim 1 wherein the input is a two-dimensional X-ray taken when aligned by at least one measuring device assembly so that the two dimensional X-ray has the known relationship to the initial linear trajectory.

7. The method of claim 1 wherein a set of measurements are taken to discern bone contour representative of a plane containing the initial linear trajectory through use of a measurement jig connected to a guide sleeve inserted in the initial cartridge.

8. The method of claim 7 wherein the set of measurements includes measurements taken in the plane containing the initial linear trajectory.

9. The method of claim 7 wherein the set of measurements does not include measurements taken in the plane containing the initial linear trajectory but is taken in at least one nearby plane so that the set of measurements are taken to discern bone contour are representative of the plane containing the initial linear trajectory.

10. The method of claim 1 wherein obtaining at least one input with the known relationship to the initial linear trajectory includes mounting at least one measuring device assembly onto the initial assembly so that measuring device assembly engages a portion of the measuring device assembly with a portion of the guide sleeve.

11. The method of claim 1 wherein obtaining at least one input with the known relationship to the initial linear trajectory includes:
  placing an end of a measuring device assembly into the opening in the initial cartridge and precluding rotation of the end of the measuring device assembly relative to the opening in the initial cartridge; and
  the end of the measuring device assembly positioned so that a coronal to apical centerline of the end of the measuring device assembly is aligned with the initial linear trajectory.

12. The method of claim 1 wherein obtaining at least one input with the known relationship to the initial linear trajectory includes:
  placing an instrument guide into the opening in the initial cartridge and precluding rotation of the instrument guide relative to the opening in the initial cartridge; the instrument guide positioned so that an coronal to apical centerline of the instrument guide is aligned with the initial linear trajectory; and
  mounting an end of a measuring device assembly upon the instrument guide so that the measuring device assembly cannot rotate around the coronal to apical centerline of the instrument guide.

13. The method of claim 1 wherein obtaining at least one input with the known relationship to the initial linear trajectory includes using a measuring device assembly that engages at least one engagement feature present on the frame.

14. The method of claim 1 wherein obtaining at least one input with the known relationship to the initial linear trajectory includes using a measuring device assembly that engages at least one engagement feature present on the initial cartridge.

15. The method of claim 1 wherein creating the frame to position the cartridge coronal to the surgical site includes shaping the frame to make contact with at least portions of at least one tooth adjacent to the surgical site.

16. The method of claim 1 wherein creating the frame to position the cartridge coronal to the surgical site includes shaping the frame to make contact with at least portions of soft tissue in edentulous areas adjacent to the surgical site.

17. The method of claim 1 wherein creating the frame to position the cartridge coronal to the surgical site in the chamber to receive the cartridge includes creating the frame with at least two chambers to receive two cartridges each with an initial linear trajectory for an implant for a multi-implant procedure.

18. The method of claim 1 wherein creating the initial cartridge with the opening from the coronal side of the initial cartridge to the apical side of the initial cartridge uses a hexagonal opening oriented with respect to a set of inner-outer and distal-mesial axes.

19. The method of claim 1 wherein creating the initial cartridge with the opening from the coronal side of the initial cartridge to the apical side of the initial cartridge uses a hexagonal opening with an outer hex ridge oriented with respect to a set of inner-outer and distal-mesial axes.

20. The method of claim 1 wherein the opening in the initial cartridge sized to constrain the orientation of the guide sleeve so that the longitudinal axis of the coronal to apical bore in the guide sleeve is positioned co-linear with the initial linear trajectory.

21. The method of claim 1 wherein the opening in the initial cartridge sized to constrain the orientation of the guide sleeve so that the longitudinal axis of the coronal to apical bore in the guide sleeve is positioned a known non-zero offset from the initial linear trajectory.

22. The method of claim 1 wherein the surgical site is located within a mandible.

23. The method of claim 1 wherein the surgical site is located within a maxilla.

24. The method of claim 1 further comprising providing irrigation fluids through a bore in the frame, a bore in the surgical cartridge, and at least one opening in the guide sleeve whenever the drill bit is driven by a drill bit drive.

25. The method of claim 24 wherein the at least one opening in the guide sleeve is a bore that is maintained in alignment with the bore in the surgical cartridge.

26. The method of claim 24 wherein the at least one opening in the guide sleeve is a set of irrigation slots in the guide sleeve so that the guide sleeve may pass irrigation fluids to the drill bit without maintaining an orientation of the guide sleeve relative to the bore in the surgical cartridge.

27. The method of claim 24 wherein irrigation fluids are provided before the drill bit is driven by the drill bit drive and are provided until manually turned off.

28. The method of claim 24 wherein irrigation fluids are provided whenever the drill bit drive is activated.

29. The method of claim 24 wherein the bore in the frame and the bore in the surgical cartridge are sized and aligned to accept a cannula for delivery of the irrigation fluids.

30. The method of claim 29 wherein the cannula helps secure the surgical cartridge to the chamber of the frame and resists dislodgment of the surgical cartridge from the chamber without interfering with a removal of the guide sleeve from the surgical cartridge while the cannula is inserted into the surgical cartridge.

* * * * *